(12) United States Patent
Luo et al.

(10) Patent No.: US 9,226,912 B2
(45) Date of Patent: Jan. 5, 2016

(54) ACETYLTANSHINONE IIA (ATA) AS ANTICANCER AGENT

(75) Inventors: Kathy Qian Luo, Singapore (SG); Ting Yu, Singapore (SG); Hou-Wei Luo, Singapore (SG)

(73) Assignee: Nanyang Technological University, Singapore (SG)

( * ) Notice: Subject to any disclaimer, the term of this patent is extended or adjusted under 35 U.S.C. 154(b) by 59 days.

(21) Appl. No.: 14/009,431

(22) PCT Filed: Feb. 13, 2012

(86) PCT No.: PCT/SG2012/000041
§ 371 (c)(1),
(2), (4) Date: Dec. 3, 2013

(87) PCT Pub. No.: WO2012/138297
PCT Pub. Date: Oct. 11, 2012

(65) Prior Publication Data
US 2014/0080796 A1 Mar. 20, 2014

Related U.S. Application Data

(60) Provisional application No. 61/472,870, filed on Apr. 7, 2011.

(51) Int. Cl.
| | | |
|---|---|---|
| A61K 31/343 | (2006.01) | |
| C07D 307/77 | (2006.01) | |
| C07D 307/92 | (2006.01) | |
| C07D 253/00 | (2006.01) | |
| A61K 31/337 | (2006.01) | |
| A61K 45/06 | (2006.01) | |

(52) U.S. Cl.
CPC ............. *A61K 31/343* (2013.01); *A61K 31/337* (2013.01); *A61K 45/06* (2013.01); *C07D 253/00* (2013.01); *C07D 307/77* (2013.01); *C07D 307/92* (2013.01)

(58) Field of Classification Search
CPC .................................................. A61K 31/343
See application file for complete search history.

(56) References Cited

PUBLICATIONS

National Cancer Institute. "Cancer Prevention Overview (PDQ)." © 2014. Available from: <http://www.cancer.gov/cancertopics/pdq/prevention/overview/patient/page3/print >.*
Zhang, Y., et al. "Tanshinones: Sources, Pharmacokinetics and Anti-Cancer Activities." Int. J. Mol. Sci. (2012), vol. 13, pp. 13621-13666.*
Adam et al., "Nuclear Protein Import in Permeabilized Mammalian Cells Requires Soluble Cytoplasmic Factors," *The Journal of Cell Biology*, 111:807-816 (Sep. 1990).
Andersen et al, "Immunohistochemical Estrogen Receptor Determination in Paraffin-Embedded Tissue," *Cancer*, 64:1901-1908 (1989).
Baker et al., "Expression of Antioxidant Enzymes in Human Prostatic Adenocarcinoma," *The Prostate*, 32:229-233 (1997).
Baselga et al., "Novel anticancer targets: revisiting ERBB2 and discovering ERBB3," *Nature Reviews—Cancer*, 9:463-475 (Jul. 2009).
Bragado et al., "Apoptosis by cisplatin requires p53 mediated p38α MAPK activation through ROS generation," *Apoptosis*, 12:1733-1742 (2007).
Budihardjo et al., "Biochemical Pathways of Caspase Activation During Apoptosis," *Annu. Rev. Cell. Dev. Biol.*, 15:269-290 (1999).
Clarke et al., "Cellular and Molecular Pharmacology of Antiestrogen Action and Resistance," *Pharmacological Reviews*, 53(1):25-71 (2001).
Cragg et al., "Plants as a source of anti-cancer agents," *Journal of Ethno-Pharmacology*, 100:72-79 (2005).
Desagher et al., "Mitochondria as the central control point of apoptosis," *Trends in Cell Biology*, 10:369-377 (Sep. 2000).
Du et al., "Smac, a Mitochondrial Protein that Promotes Cytochrome c-Dependent Caspase Activation by Eliminating IAP Inhibition," *Cell*, 102:33-42 (Jul. 7, 2000).
Finucane et al., "Bax-induced Caspase Activation and Apoptosis via Cytochrome *c* Release from Mitochondria is Inhibitable by Bcl-xL," *The Journal of Biological Chemistry*, 274(4):2225-2233 (1999).
Gordaliza "Natural products as leads to anticancer drugs," *Clin Transl Oncol*, 9:767-776 (2007).
Green et al., "Oestrogen-receptor-mediated transcription and the influence of co-factors and chromatin state," *Nature Reviews—Cancer*, 7:713-722 (2007).
Hao et al., "Identification of a Novel Intestinal First Pass Metabolic Pathway: NQO1 Mediated Quinone Reduction and Subsequent Glucuronidation," *Current Drug Metabolism*, 8:137-149 (2007).
Hoskins et al., "CYP2D6 and tamoxifen: DNA matters in breast cancer," *Nature*, 9:576-586 (Aug. 2009).
Howell et al., "Response to a specific antioestrogen (ICI 182780) in tamoxifen-resistant breast cancer," *The Lancet*, 345:29-30 (Jan. 7, 1995).
Hug et al., "Reactive Oxygen Intermediates are Involved in the Induction of CD95 Ligand mRNA Expression by Cytostatic Drugs in Hepatoma Cells," *The Journal of Biological Chemistry*, 272(45):28191-28193 (1997).

(Continued)

*Primary Examiner* — Andrew D Kosar
*Assistant Examiner* — John S Kenyon
(74) *Attorney, Agent, or Firm* — Seed IP Law Group PLLC

(57) ABSTRACT

The present invention relates to the use of a compound of Formula I for the manufacture of a medicament for treating or preventing cancer in a subject. Formula I

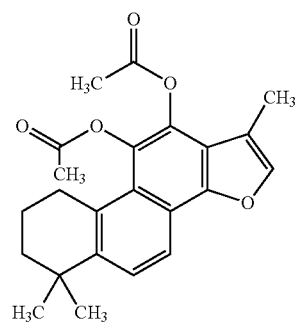

Formula I

19 Claims, 25 Drawing Sheets

(56) References Cited

PUBLICATIONS

Jang et al., "Study on Dehydration Mechanism of Tanshinones in Mass Spectral Fragmentation," *Journal of China Pharmaceutical University*, 19(3):197-200 (1988).

Jing et al., "Arsenic Trioxide Selectively Induces Acute Promyelocytic Leukemia Cell Apoptosis Via a Hydrogen Peroxide-Dependent Pathway," *Blood*, 94(6):2102-2111 (1999).

Kim et al., "Doxorubicin-induced reactive oxygen species generation and intracellular $Ca^{2+}$ increase are reciprocally modulated in rat cardiomyocytes," *Experimental and Molecular Medicine*, 38(5):535-545 (Oct. 2006).

Lau et al., "Reactive Oxygen Species: Current Knowledge and Applications in Cancer Research and Therapeutic," *Journal of Cellular Biochemistry*, 104:657-667 (2008).

Lee et al., "Reactive oxygen species-mediated kinase activation by dihydrotanshinone in tanshinones-induced apoptosis in HepG2 cells," *Cancer Letters*, 285:46-57 (2009).

Li et al., "Cytochrome c and dATP-Dependent Formation of Apaf-1/Caspase-9 Complex Initiates an Apoptotic Protease Cascade," *Cell*, 91:479-489 (Nov. 14, 1997).

Liu et al. "Induction of apoptosis and inhibition of cell adhesive and invasive effects by tanshinone IIA in actue promyelocytic leukimia cells *in vitro*," *Journal of Biomedical Science*, 13:813-823 (2006).

Luo et al., "Relationship Between Structure and Antibacterial Activities of Tanshinones and Related Compounds," *Journal of China Pharmaceutical University*, 19(4):258-262 (1988) (Abstract).

Luo et al., "Application of the Fluorescence Resonance Energy Transfer Method for Studying the Dynamics of Caspase-3 Activation during UV-Induced Apoptosis in Living HeLa Cells," *Biochemical and Biophysical Research Communications*, 283:1054-1060 (2001).

Luo et al., "The gene-silencing efficiency of siRNA is strongly dependent on the local structure of mRNA at the targeted region," *Biochemical and Biophysical Research Communications*, 318:303-310 (2004).

Massarweh et al. "Unraveling the Mechanisms of Endocrine Resistance in Breast Cancer: New Therapeutic Opportunities," *Clin Cancer Res*, 13(7):1950-1954 (Apr. 1, 2007).

Mizutani et al. "Distinct mechanisms of the site-specific oxidative DNA damage by doxorubicin in the presence of copper(II) and NADPH-cytochrome P450 reductase," *Cancer Sci*, 94(8):686-691 (Aug. 2003).

Nadji et al , "Immunohistochemistry of Estrogen and Progesterone Receptors Reconsidered," *Am J Clin pathol*, 123:21-27 (2005).

Newman et al., "Natural Products as Sources of New Drugs over the Last 25 Years," *J. Nat. Prod.*, 70:461-477 (2007).

Oberley et al., "Role of Superoxide Dismutase in Cancer: A Review," *Cancer Research*, 39:1141-1149 (Apr. 1979).

Oberley et al., "Antioxidant enzyme levels in cancer," *Histology and Histopathology*, 12:525-535 (1997).

Ono et al., "Molecular Mechanisms of Epidermal Growth Factor Receptor (EGFR) Activation and Response to Gefitinib and Other EGFR-Targeting Drugs," *Clin Cancer Res*, 12(24):7242-7251 (Dec. 15, 2006).

Pohlmann et al., "Resistance to Trastuzumab in Breast Cancer," *Clin Cancer Res*, 15(24):7479-7491 (Dec. 15, 2009).

Porter et al., "Emerging roles of caspase-3 in apoptosis," *Cell Death and Differentiation*, 6:99-104 (1999).

Stierer et al , "Immunohistochemical and Biochemical Measurement of Estrogen and Progesterone Receptors in Primary Breast Cancer," *Annals of Surgery*, 218(1):13-21 (1993).

Su et al., Tanshinone IIA down-regulates the protein expression of ErbB-2 and up-regulates TNF-*a* in colon cancer cells *in vitro* and *in vivo*, *International Journal of Molecular Medicine*, 22:847-851 (2008).

Sun et al., "Synthesis of Some Compounds Related to Tanshinquinone," *Acta Pharmaceutica Sinica*, 20(1):39-43 (1985).

Sun, "Free Radicals, Antioxidant Enzymes, and Carcinogenesis," *Free Radical Biology & Medicine*, 8:583-599 (1990).

Sung et al., "Tanshinone IIA, an ingredient of *Salvia miltiorrhiza* BUNGE, induces apoptosis in human leukemia cell lines through the activation of caspase-3," *Experimental and Molecular Medicine*, 31(4):174-178 (Dec. 1999).

Szatrowski et al., "Production of Large Amounts of Hydrogen Peroxide by Human Tumor Cells," *Cancer Research*, 51:794-798 (Feb. 1, 1991).

Tian et al., "A high throughput drug screen based on fluorescence resonance energy transfer (FRET) for anticancer activity of compounds from herbal medicine," *British Journal of Pharmacology*, 150:321-334 (2007).

Tian et al. "A novel compound modified from tanshinone inhibits tumor growth *in vivo* via activation of the intrinsic apoptotic pathway," *Cancer Letters*, 297:18-30 (2010).

Tsang et al., "Reactive oxygen species mediate doxorubicin induced p53-independent apoptosis," *Life Sciences*, 73:2047-2058 (2003).

Vichai et al., "Sulforhodamine B colorimetric assay for cytotoxicity screening," *Nature Protocols*, 1(3):1112-1116 (2006).

Wang et al., "Growth inhibition and induction of apoptosis and differentiation of tanshinone IIA in human glioma cells," *J Neurooncol*, 82:11-21 (2007).

Wang "The expanding role of mitochondria in apoptosis," *Genes & Development*, 15:2922-2933 (2001).

Wang et al., "New Developments in the Chemistry and Biology of the Bioactive Constituents of Tanshen," *Medicinal Research Reviews*, 27(1):133-148 (2007).

Wang et al. "Potential anticancer activity of tanshinone IIA against human breast cancer," *Int. J. Cancer*, 116:799-807 (2005).

Wen et al., "HER2 signaling modulates the equilibrium between pro- and antiangiogenic factors via distinct pathways: implications for HER2-targeted antibody therapy," *Oncogene*, 25:6986-6996 (2006).

Wu et al., "Cytotoxic Activities of Tanshinones Against Human Carcinoma Cell Lines," *American Journal of Chinese Medicine*, XIX(3-4):207-216 (1991).

Xia et al., "Antioxidant therapy with Salvia miltiorrhiza decreases plasma endothelin-1 and thromboxane B2 after cardiopulmonary bypass in patients with congenital heart disease," *The Journal of Thoracic and Cardiovascular Surgery*, 126:1404-1410 (2003).

Yu et al., "Overexpression of ErbB2 in cancer and ErbB2-targeting strategies," *Oncogene*, 19:6115-6121 (2000).

Yuan et al., "Reversing effect of Tanshinone on malignant phenotypes of human hepatocarcinoma cell line," *WJG*, 4(4):153-157 (1998).

* cited by examiner

Tanshinone IIA = TIIA
MW = 294.13

Acetyltanshinone IIA = ATA
MW = 380.16

A

B

ACETYLTANSHINONE IIA (ATA) AS ANTICANCER AGENT

CROSS-REFERENCE TO RELATED APPLICATIONS

This application claims the benefit of priority of U.S. provisional application No. 61/472,870, 2011, filed Apr. 7, 2011, the content of it being hereby incorporated by reference in its entirety for all purposes.

FIELD OF THE INVENTION

The present invention lies in the field of anti-cancer therapy and particularly relates to the treatment and prevention of various types of cancer, including breast cancer, by use of acetyltanshinone IIA (ATA). The invention further relates to methods of inducing apoptosis or interfering with estrogen receptor signaling in cells by use of ATA.

BACKGROUND

Breast cancer is the second most common type of cancer and related mortality in women in most countries causing 519,000 deaths worldwide in 2004 alone. Two main types of breast cancer are estrogen receptor (ER) positive cancers, wherein ER is over-expressed, and HER2 positive cancers, wherein human epidermal growth factor 2 (HER2) is overexpressed compared to normal breast tissue cells (M. Nadji, C. Gomez-Fernandez, P. Ganjei-Azar, A. R. Morales, Immunohistochemistry of estrogen and progesterone receptors reconsidered: experience with 5,993 breast cancers. Am J Clin Pathol 123 (2005) 21-27). The majority of breast cancers is ER-positive and requires estrogen for growth and progression. The binding of estrogen to ER changes its conformation and leads to the release of the receptor from heat shock proteins (HSPs), the release promoting dimer formation of the ER monomers. The dimerized ERs recruit their co-activators to stimulate target gene expression. Encoded proteins can promote cell division, resulting in fast proliferation and metastasis (K. A. Green, J. S. Carroll, Oestrogen-receptor-mediated transcription and the influence of co-factors and chromatin state. Nat Rev Cancer 7 (2007) 713-722) (FIG. 1).

Overexpression of the HER2 receptor in breast cancer cells is associated with increased disease recurrence and worse prognosis. HER2 is a cell membrane surface-bound receptor tyrosine kinase and is normally involved in the signal transduction pathways leading to cell growth and differentiation. It is encoded by HER2/neu, a known proto-oncogene. HER2 is thought to be an orphan receptor, with none of the EGF family of ligands able to activate it. However, other ErbB receptors dimerise on ligand binding, and HER2 is the preferential dimerization partner of other members of the ErbB family.

Currently, the most commonly used drug for treating ER-positive breast cancer is tamoxifen, which can bind to ER and inhibit its binding to the receptor's co-activators, therefore preventing target gene transcription. Although tamoxifen is very effective in treating ER-positive breast cancer, it has limitations. First, tamoxifen is not effective in about 30% of breast cancer patients. Second, tamoxifen resistance has been observed in 80% of patients after 15 months of treatment (A. Howell, D. DeFriend, J. Robertson, R. Blamey, P. Walton, Response to a specific antioestrogen (ICI-182780) in tamoxifen-resistant breast cancer. Lancet 345 (1995) 29-30). Third, clinical evidence suggests that cells overexpressing HER2 are more likely to become tamoxifen resistant. Although therapies that target HER2 have been developed, including trastuzumab, a monoclonal antibody, and lapatinib, a tyrosine kinase inhibitor, the available therapies are very expensive and resistance to these drugs has been reported as well.

Thus, there is still need for alternative treatment regimens for breast cancer that overcome the known problems.

SUMMARY OF THE INVENTION

The present invention is based on the inventors finding that acetyltanshinone IIA (ATA) can act as an anti-cancer agent and thus has use in the treatment or prevention of cancer, in particular breast cancer. As it has been surprisingly found that ATA interferes with ER signaling and is particularly effective in estrogen-positive breast cancer, ATA provides a new approach for treating cancers that do not respond to tamoxifen therapy. The usefulness of ATA has been further confirmed by the unexpected finding that ATA also interferes with HER2 expression.

Thus, in a first aspect, the present invention relates to a method for treating or preventing cancer in a subject, comprising administering an effective amount of acetyltanshinone IIA (ATA) to the subject in need thereof. The structure of acetyltanshinone IIA (ATA) is depicted in Formula I.

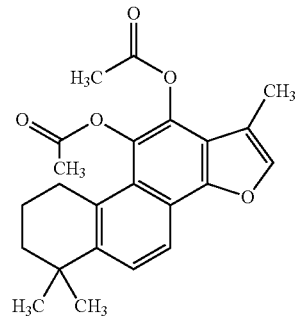

Formula I

In a further aspect, the present invention relates to the use of a compound of Formula I

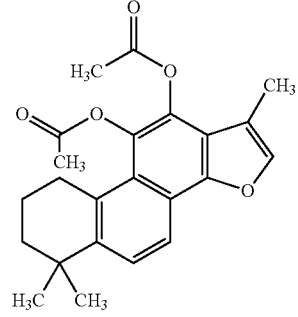

Formula I for the manufacture of a medicament for treating or preventing cancer in a subject. This use comprises administering a therapeutically effective amount of said compound to said subject.

In yet another aspect, the present invention relates to a compound of Formula I

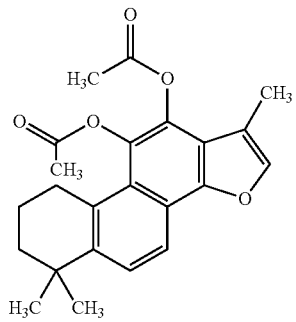

Formula I for use in the manufacture of a medicament for treating or preventing cancer in a subject.

In various embodiments, the cancer treated or prevented is breast cancer, preferably ER positive and/or HER2 positive cancer.

Thus, in a further aspect, the present invention relates to the use of a compound of Formula I for the manufacture of a medicament for treating or preventing estrogen receptor positive (ER+) breast cancer in a subject. This use comprises administering a therapeutically effective amount of said compound to said subject.

In yet another aspect, the present invention relates to a method for inhibiting estrogen receptor signaling in a cell, comprising contacting said cell with an effective amount of a compound of Formula I.

In still another aspect, the present invention relates to a method for reducing HER2 levels in a cell, comprising contacting said cell with an effective amount of a compound of Formula I.

In a further aspect, the present invention relates a method for inducing apoptosis in a cell, comprising contacting said cell with an effective amount of a compound of Formula I.

Furthermore, the present invention relates in another aspect to a method for the synthesis of a compound of Formula I comprising the steps of:
(a) adding tanshinone IIA (1,6,6-trimethyl-8,9-dihydro-7H-naphtho[1,2-g][1]benzofuran-10,11-dione), an acetate salt and anhydrous zinc powder to acetic anhydride to provide a reaction mixture;
(b) heating the reaction mixture;
(c) filtrating the reaction mixture to remove insoluble residues;
(d) adding water to the filtrate and heating the resulting solution;
(e) filtering the resulting solution to obtain the compound of Formula I as a solid.

The present invention allows the application of acetyltanshinone IIA (ATA) as a new anticancer agent. Moreover, it allows the application of ATA in the treatment of breast cancer overexpressing the estrogen receptor (ER) and/or the human epidermal receptor 2 (HER2).

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
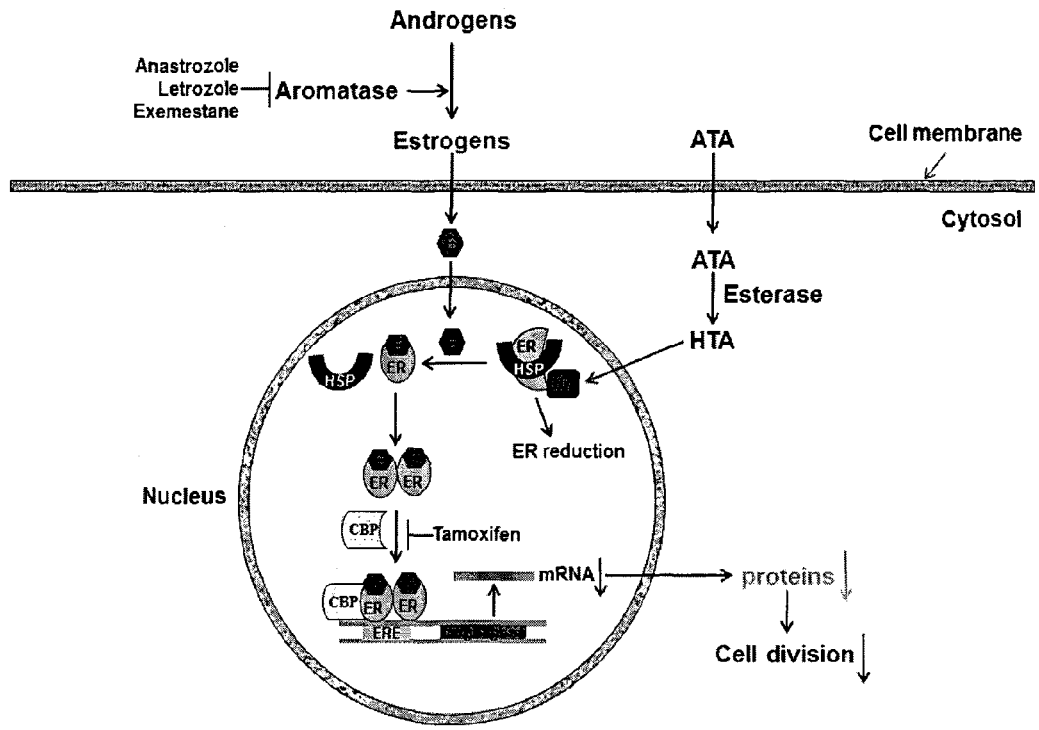
FIG. 1 schematically illustrates the principle of the estrogen-dependent signaling pathway of ER activation and mechanisms of ATA in inhibiting ER-positive cell growth.

The dry root of *Alvia miliorrhiza* Bunge also known as Danshen is traditionally used in China to treat diseases such as hepatitis and heart disease. Over 40 lipid-soluble tanshinone compounds have been isolated from this root among which tanshinone IIA, tanshinone I and cryptotanshinone are the major constituents.

The inventors of the present invention have now surprisingly discovered that acetyltanshinone IIA (ATA), obtained by chemical modification of tanshinone TIIA (TIIA) (FIG. 2), exhibits anti-cancer effects and thus may be used as an anti-cancer agent for treating or preventing cancer in a subject. Further, the inventors have demonstrated that ATA has a strong cytotoxicity on multiple cancer cell lines, but is less toxic to normal, non-cancer cells including breast, muscle and fibroblast cells.

In a first aspect, the present invention thus relates to a method for treating or preventing cancer in a subject, comprising administering an effective amount of a compound of Formula I.

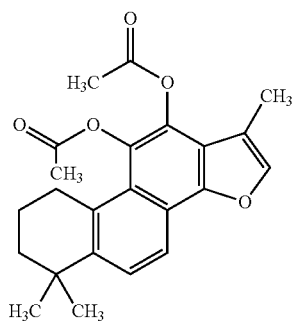

Formula I

In various embodiments of this aspect of the present invention the cancer is selected from breast cancer, cervical cancer, lung cancer, liver cancer, colorectal adenocarcinoma, neuroblastoma, melanoma, and leukemia.

In various embodiments of this aspect of the present invention the cancer is estrogen receptor-positive (ER+) breast cancer. In recent years, much progress has been made in the field of individualized medicine and individualized cancer treatment. In particular, it has been found that each cancer may require a specifically tailored therapy that takes into account molecular changes in the cancer, as certain aberrations in expression levels and protein activity may render the cancer more susceptible or more resistant to a specific treatment. The finding that a specific subclass of breast cancer is particularly susceptible to treatment with ATA, as claimed herein, is thus highly significant, as it can help to circumvent problems connected to resistance to other conventional treatment forms, such as tamoxifen treatment.

ATA is especially useful for breast cancer patients lacking the enzyme cytochrome P450 2D6. This enzyme converts the standard anti-ER+ breast cancer drug tamoxifen to its active metabolite endoxifen. Among healthy Europeans 6-10% of individuals are deficient in CYP2D6. These patients convert tamoxifen to endoxifen poorly and therefore may not derive full therapeutic benefit from its in FIG. 4 ATA can be used as an alternative therapy in these patients as it shows a significantly higher growth inhibition rate than tamoxifen in breast cancer cell.

The term "estrogen receptor positive (ER+) breast cancer" as used herein refers to breast cancer cells that overexpress the estrogen receptor compared to normal cells and breast cancer cells which do not show elevated levels of the estrogen receptor. "Estrogen receptor" or "ER" refers to a receptor that is activated by the hormone 17β-estradiol (estrogen). ER is a member of the nuclear receptor family. The main function of the estrogen receptor is as a DNA-binding transcription factor that regulates gene expression. In the absence of hormone, estrogen receptors are sequestered by the heat shook proteins (HSP) located in the nucleus. Hormone binding to the receptor triggers a number of events starting with disassociation from HSP, dimerization of the receptor, and subsequent binding of the receptor dimer to co-activators. The ER/co-activator complex then binds to hormone response elements in the DNA then recruits other proteins that are responsible for the transcription of downstream DNA into mRNA and finally protein that results in a change in cell function.

The term "overexpression" as used herein, refers to a gene expression that is higher than endogenous expression of the same or related gene in the same cell or tissue in its non-diseased state. In certain embodiments, overexpression of a gene results in at least 1.5 fold, 2 fold, or 2.5 fold increase of the gene product compared to levels in normal, undiseased cells.

The term "therapeutically effective amount" as used herein refers to the amount of the compound of Formula I required to treat or prevent estrogen receptor positive (ER+) breast cancer in a given subject either alone or in combination with one or more other active agents. Effective amounts vary, as recognized by those skilled in the art, depending, inter alia, on route of administration, excipient usage and co-usage with other active agents as well as age, weight other diseases and subject specific side effects. The therapeutically effective amount for a given situation can be readily determined by routine experimentation and is within the skill and judgment of the ordinary clinician.

The term "administer" or "administration, as used herein, refers to the application of the respective compound with or without further additives, such as pharmaceutical carriers, to a subject in need thereof. The routes of administration of the compound either alone or in combination with other substances may be by any medically acceptable means, including, but not limited to oral, subcutaneous, intramuscular, intravenous, intra-arterial, sublingual, buccal, rectal, peritoneal, nasal, transdermal, transmucosal, vaginal, transurethral, iontophoretic, and by inhalation. The compounds may be administered enterally (e.g., orally or rectally) or parenterally (e.g., by subcutaneous, intravenous, intramuscular, intrasternal, or peritoneal injection or infusion techniques) in dosage formulations containing conventional pharmaceutically acceptable carriers, adjuvants, and vehicles as desired. The compounds may be delivered locally, as to portions of the gastrointestinal tract. Additional methods of administration are known in the art.

The compound either alone or in combination with other substances can be administered in solid form or in liquid form. The compound can be administered in the form of tablets, pills, powder mixtures, capsules, granules, injectables, creams, solutions, suppositories, enemas, colonic irrigations, emulsions, dispersions, food premixes, animal feed, and in other suitable forms.

The compound of Formula I either alone or in combination with other substances may also be formulated as sustained release or delayed release formulations as well as injectable preparations.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

The frequency and duration of administration of the compound of Formula I either alone or in combination with other substances will depend on the condition of the individual, and the like. The compound of Formula I either alone or in combination with other substances may be administered to the individual one or more times, for example, 2, 3, 4, 5, 10, 15, 20, 50, 75, 100, or more times. The formulation may be administered to the individual, for example, once a day, two times a day, three times a day, or more than three times a day. The formulation may also be administered to the individual, for example, less than once a day, for example, every other day, every third day, every week, or less frequently. The formulation may be administered over a period of days, weeks, months, years, or chronically, such as life-long administration. The determination of dose and frequency of administration lie within the capability of the responsible physician.

In various embodiments of this aspect of the present invention the cancer is HER2 positive (HER2+) breast cancer.

In addition to the type of breast cancer that over-expresses estrogen receptor, another subclass of breast cancers are those that over-expresses human epidermal growth factor receptor 2 (HER2). HER2 over-expression has been detected in nearly 30% of breast cancers and patients with a high level of HER2 are usually found resistance to tamoxifen therapy. HER2 is also known as proto-oncogene Neu, receptor tyrosine-protein kinase erbB-2, CD340 or p185. HER2 is a protein that in humans is encoded by the ERBB2 gene. It is a member of the ErbB protein family, more commonly known as the epidermal growth factor receptor family. HER2 is a cell membrane surface-bound receptor tyrosine kinase and is normally involved in the signal transduction pathways leading to cell growth and differentiation. HER2 is thought to be an orphan receptor, with none of the EGF family of ligands able to activate it. However, as already disclosed supra, ErbB receptors dimerize on ligand binding, and HER2 is the preferential dimerization partner of other members of the ErbB family. In clinical usage, HER2/neu is important as the target of the monoclonal antibody trastuzumab (marketed as Herceptin). Trastuzumab is effective only in cancers where the HER2/neu receptor is overexpressed. One of the mechanisms of how trastuzumab works after it binds to HER2 is by increasing p27, a protein that halts cell proliferation. Another monoclonal antibody, Pertuzumab, which inhibits dimerization of HER2 and HER3 receptors, is in advanced clinical trials. The expression of HER2/ERBB2 protein is regulated by estrogen receptors. Furthermore, estradiol and tamoxifen acting through the estrogen receptor normally down-regulates the expression of HER2/ERBB2. However, in a certain subgroup of patients, the expression of HER2/ERBB2 is upregulated in the presence of tamoxifen, leading to tamoxifen-resistant breast cancer.

The inventors of the present invention have shown for the first time that ATA is more effective in inhibiting the growth of breast cancer cells with high level of HER2. This is significant, as it not only marks the subclass of breast cancers that overexpress HER2 for being particularly susceptible to treatment with ATA, but also underlines the usefulness of ATA in treating ER overexpressing breast cancers that are resistant to tamoxifen therapy. In certain embodiments of the present invention, the cancer treated is thus breast cancer that over-expresses estrogen receptor as well as HER2 (ER+/HER2+ breast cancer). The term "estrogen receptor positive/HER2 positive (ER+/HER2+) breast cancer", as used herein, thus refers to breast cancer cells that overexpress both the estrogen and the human epidermal growth factor receptor 2 (HER2) compared to breast cancer cells or normal breast tissue cells, which do not show elevated levels of both, the estrogen receptor and the human epidermal growth factor receptor 2.

In various embodiments of the present invention, the method further comprises administering a second anticancer agent to the subject.

The term "second anticancer agent" as used herein refers to an agent other than the compound of Formula I useful in the treatment or prevention of cancer, e.g., due to its capability to kill rapidly dividing cells, to inhibit or slow down cell division or to act against abnormal proteins.

In various embodiments of this aspect of the present invention the second anticancer agent is administered before, together with or after the compound of Formula I. These different modes of administration may be, inter alia, useful for reduction of side effect and increasing bioavailability and/or patient compliance.

In various embodiments of this aspect of the present invention the second anticancer agent is selected from the group consisting of paclitaxel, doxorubicin, herceptin, lapatinib, gefitinib, erlotinib, tamoxifen, fulvestrant, anastrazole, lectrozole, exemestane, fadrozole and combinations thereof. In case such combination therapy is used, the cancer may be breast cancer, for example ER+ breast cancer.

In various embodiments of this aspect of the present invention the subject has prior to administration of the compound of Formula I underwent anticancer therapy with a different anticancer agent or anticancer agent combination.

In various embodiments of this aspect of the present invention the subject has previously been treated with an anticancer agent selected from the group of selective estrogen receptor modulators, estrogen receptor down regulators, aromatase inhibitors, HER2 inhibitors, anthracyclines, and combinations thereof. In various embodiments of this aspect of the present invention the anticancer agent used in the earlier treatment of the subject is selected from the group consisting of doxorubicine, paclitaxel, herceptin, lapatinib, gefitinib, erlotinib, tamoxifen, fulvestrant, anastrazole, lectrozole, exemestane, fadrozole and combinations thereof.

According to one embodiment of this aspect of the present invention the subject has failed the previous therapy. The term "failed the previous therapy" as used herein refers to the situation that previous therapy has proven not to be useful for a particular subject, for example, because the subject did not respond as expected to the previous therapy or the previous therapy showed side effects too severe in that particular subject for the treatment to be continued.

The previous therapy may, inter alia, include earlier chemotherapy, for example by treatment of one of the above-listed known anticancer agents, but may also have been radiation therapy and/or surgery.

In various embodiments of this aspect of the present invention the subject has developed resistance to one or more of the previously used anticancer agents.

As used herein the term "resistance" refers to reduction in effectiveness of a treatment, e.g. a drug, in curing cancer, leading to the said treatment no longer considered helpful or no longer considered the best available treatment for the patient in question.

In other embodiments, the treatment with ATA, as disclosed herein, is used in combination with other cancer treatment strategies, such as surgical intervention, radiation therapy or therapy with another anticancer agent, to enhance the effectiveness of this conventional treatment form.

In various embodiments of this aspect of the present invention the subject is a mammal.

In various embodiments of this aspect of the present invention the subject is a human.

In another aspect, the present invention is directed at the use of a compound of Formula I for the manufacture of a medicament for treating or preventing estrogen receptor positive (ER+) breast cancer in a subject. This use may comprise administering a therapeutically effective amount of said compound to said subject.

In various embodiments of the current invention the breast cancer is estrogen receptor positive/HER2 positive (ER+/HER2+) breast cancer.

In various embodiments of the current invention the use further comprises administering a second anticancer agent to said subject.

In various embodiments of the current invention the second anticancer agent is administered before, together with or after the compound of Formula I. In various embodiments of the current invention the second anticancer agent is selected from the group consisting of paclitaxel, doxorubicin, herceptin, lapatinib, gefitinib, erlotinib, tamoxifen, fulvestrant, anastrazole, lectrozole, exemestane, fadrozole and combinations thereof.

As recognized by those skilled in the art all of these agents are reliable and well tested anti-cancer agents.

In various embodiments of the current invention the subject has underwent anticancer therapy with a different anticancer agent or anticancer agent combination prior to administration of the compound of Formula I.

The invention also encompasses the use of a compound of Formula I, wherein the subject has previously been treated with an anticancer agent selected from the group of selective estrogen receptor modulators, estrogen receptor down regulators, aromatase inhibitors, HER2 inhibitors, anthracyclines, and combinations thereof. In various embodiments of the current invention, wherein the subject has previously been treated with an anticancer agent this anticancer agent is selected from the group consisting of paclitaxel, doxorubicin, herceptin, lapatinib, gefitinib, erlotinib, tamoxifen, fulvestrant, anastrazole, lectrozole, exemestane, fadrozole and combinations thereof. In various embodiments of the current invention the subject has failed the previous therapy. In various embodiments of the current invention the subject has developed resistance to one or more of the previously administered anticancer agents.

The specific embodiments disclosed above in connection with the methods of treating cancer, are similarly applicable to the claimed uses.

In still another aspect, the present invention relates to a method for inhibiting estrogen receptor signaling in a cell, comprising contacting said cell with an effective amount of a compound of Formula I. The method may be an in vivo or an in vitro method. "In vitro method", in this connection refers to embodiments where the cells are no longer present in a living organism, but are, for example, cultured.

In various embodiments of the claimed method for inhibiting estrogen receptor signaling in a cell, the estrogen receptor signaling is inhibited by binding of the compound of Formula I to estrogen receptors located in the nucleus or in the cytosol. Since estrogen is a steroidal hormone, it can pass through the phospholipid membranes of the cell, and receptors therefore do not need to be membrane-bound in order to bind with estrogen. The binding of, for example, the estrogen hormone to the receptor triggers a number of events starting with disassociation from heat shock proteins, dimerization of the receptor, and subsequent binding of the receptor dimer to co-activators. The ER/co-activator complex then binds to hormone response elements in the DNA then recruits other proteins that are responsible for the transcription of downstream DNA into mRNA and finally protein that results in a change in cell function.

The term "complex" as used herein refers to a multiprotein complex, i.e., a group of two or more associated polypeptide chains.

In various embodiments of the present invention the estrogen receptor signaling is inhibited by down-regulating ERα level through both promoting estrogen receptor protein degradation and reducing the mRNA levels of ERα. The reduced ERα protein level then leads to reduced level of estrogen receptor-responsive gene expression.

As used herein, "level" relates to the concentration of a given agent. Down-regulating a protein level can for example occur by interfering with the expression of the gene encoding said protein or directly targeting the protein, for example by use of neutralizing antibodies or degrading enzymes. Down-regulating a gene can be achieved by inhibiting its expression.

When used in relation to a gene, the term "level" generally relates to the expression level of said gene. When used in relation to a protein, the term "level" relates to the concentration of said protein, for example the cellular concentration.

As used herein the term "protein degradation" refers to the directed digestion of proteins usually by enzymes via proteolysis, which breaks the peptide bonds that link amino acids together in the polypeptide chain forming the protein. However, protein degradation may also occur via other mechanisms breaking the peptide bonds such as heat and pH-value changes.

As used herein the term "reduced mRNA levels" refers to levels of messenger RNA (mRNA), which are lower than those prior to inhibition of the estrogen receptor signaling.

As used herein the term "receptor-responsive gene expression" refers to gene expression, i.e. the process by which information from a gene is used in the synthesis of a functional gene product, as result of the interaction with a receptor. Functional gene products are usually proteins, but in certain cases may be RNA molecules.

In still another aspect the present invention relates to a method for reducing HER2 expression in a cell, comprising contacting said cell with an effective amount of a compound of Formula I.

The term "reducing HER2 expression" as used herein refers to a decrease in levels of HER2 (human epidermal growth factor receptor 2).

In yet a further aspect the present invention relates a method for inducing apoptosis in a cell, comprising contacting said cell with an effective amount of a compound of Formula I.

The term "apoptosis" as used herein refers to the process of programmed cell death, as it is known and understood by those skilled in the art. Usually, in apoptosis biochemical events lead to characteristic cell changes and death. These changes include blebbing, cell shrinkage, nuclear fragmentation, chromatin condensation, and chromosomal DNA fragmentation. Typically, apoptosis produces cell fragments called apoptotic bodies that phagocytic cells are able to engulf and quickly remove before the contents of the cell can spill out onto surrounding cells and cause damage to these.

In various embodiments of the present invention apoptosis is induced by generation of reactive oxygen species.

As used herein the term "reactive oxygen species" refers to chemically reactive molecules containing oxygen. Reactive oxygen species (ROS) are highly reactive due to the presence of unpaired valence shell electrons. ROS form as a natural byproduct of the normal metabolism of oxygen and have important roles in cell signaling and homeostasis. Examples of reactive oxygen species include oxygen ions and peroxides. During times of environmental stress (e.g., UV or heat exposure), ROS levels can increase dramatically. This may result in significant damage to cell structures. This cumulates into a situation known as oxidative stress. ROS are also generated by exogenous sources such as ionizing radiation.

The inventors of the present invention have found that ATA induces ROS generation, which leads to apoptosis in cancer cells.

Furthermore the present invention relates to a method for the synthesis of a compound of Formula I, i.e. ATA, comprising the steps of:
  (a) adding tanshinone IIA (1,6,6-trimethyl-8,9-dihydro-7H-naphtho[1,2-g][1]benzofuran-10,11-dione), an acetate salt and anhydrous zinc powder to acetic anhydride to provide a reaction mixture;
  (b) heating the reaction mixture;

(c) filtrating the reaction mixture to remove insoluble residues;
(d) adding water to the filtrate and heating the resulting solution;
(e) filtering the resulting solution to obtain the compound of Formula I as a solid.

The term "filtration" as used herein refers to the process of separating solids from fluids (liquids or gases) by interposing a medium through which only the fluid can pass.

In various embodiments of the present invention the acetate salt is alkali metal acetate, such as sodium acetate or potassium acetate.

In various embodiments of the present invention step (b) comprises heating to about 80-120° C., for example 100° C. for several hours, for example about 1 to 5 hours, or about 3 hours. In various embodiments of this aspect of the present invention, step (d) comprises heating to about 80-120° C., for example 100° C.

In various embodiments of the present invention the method further comprises recrystallizing the solid product in 95% ethanol.

Figure 2:
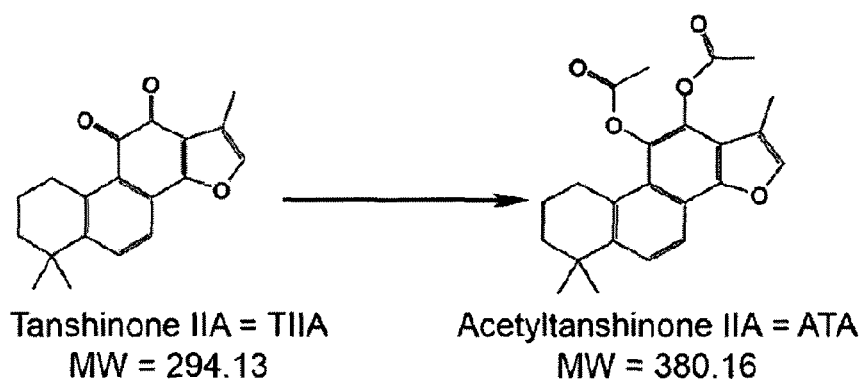
FIG. 2 depicts the structures of tanshinone IIA (TIIA, C19H18O3) and acetyltanshinone IIA (ATA, C23H24O5).

In one specific embodiment of this aspect, ATA is synthesized as follows:

A mixture of TIIA (2.04 g), sodium acetate (2.5 g), acetic anhydride (18 ml), and anhydrous zinc powder (6 g) is stirred in a boiling water bath for 3 h, then immediately filtrated by using a vacuum filtration system to remove the insoluble residues. The filtrate is diluted with water (300 ml), and then heated to boil. The resulting solution is cooled at room temperature and filtered to give a solid product (1.80 g). The product can be further crystallized using 95% ethanol to produce the final product (1.51 g) acetyltanshinone IIA (ATA) with chemical designation of 1,6,6-trimethyl-8,9-dihydro-10,11-diacetoxyl-7H-naphtho[1,2-g][1]benzofuran (FIG. 2). ATA appeared in white color, which is totally different from its original red color. ATA has a 22-fold higher solubility in both DMSO and PBS than TIIA.

Mass spectrometry and nuclear magnetic resonance can be used to verify the production of the compound.

Thus, the present invention provides for the compound ATA which can be used to treat cancer, especially
  breast cancer expressing ER, which accounts for 60-70% of all cases;
  breast cancer exhibiting high levels of HER2 protein, which account for 20-30% of all cases;
  breast cancer patients lacking the enzyme cytochrome P450 2D6;
  breast cancer that are not responsive to tamoxifen treatment, these are about 30% of all cases;
  breast cancers that develop resistance to tamoxifen, as it is the case in about 80% of all patients after 15 months of tamoxifen treatment;
  breast cancers that develop resistance to tamoxifen due to HER2 overexpression.

Other embodiments are within the following non-limiting examples.

EXAMPLES

Example 1

Cytotoxicity of ATA in Multiple Cancer Cell Lines

To compare the anticancer efficacy of ATA among various cancer cell lines, the concentration of ATA to inhibit 50% of cell growth ($IC_{50}$) or kill 50% of the cells ($LC_{50}$) after 48 h of treatment was measured. As demonstrated in Table 1, ATA showed a broad spectrum of growth inhibition and cytotoxicity against all six cancer cell lines derived from breast cancer, cervical cancer, melanoma and leukemia.

TABLE 1

$IC_{50}$ and $LC_{50}$ values of ATA at 48 h on various cancer and non-cancer cell lines

| Cell types | Cell line | $IC_{50}$ (μM) | $LC_{50}$ (μM) |
|---|---|---|---|
| Breast cancer | SK-BR-3 | 0.29 ± 0.25 | 5.10 ± 1.92 |
|  | MCF-7 | 1.39 ± 0.64 | 7.64 ± 0.30 |
| Melanoma | MDA-MB-435 | 0.55 ± 0.15 | 2.74 ± 0.51 |
| Leukemia | HL-60 | 2.98 ± 0.37 | 8.53 ± 0.20 |
| Cervical cancer | HeLa | 1.39 ± 0.13 | 10.91 ± 1.45 |
|  | SiHa | 1.96 ± 0.49 | 12.32 ± 0.68 |
| Non-cancer breast cell line | MCF-10A | 6.64 ± 1.15 | 16.27 ± 4.46 |

Figure 12:
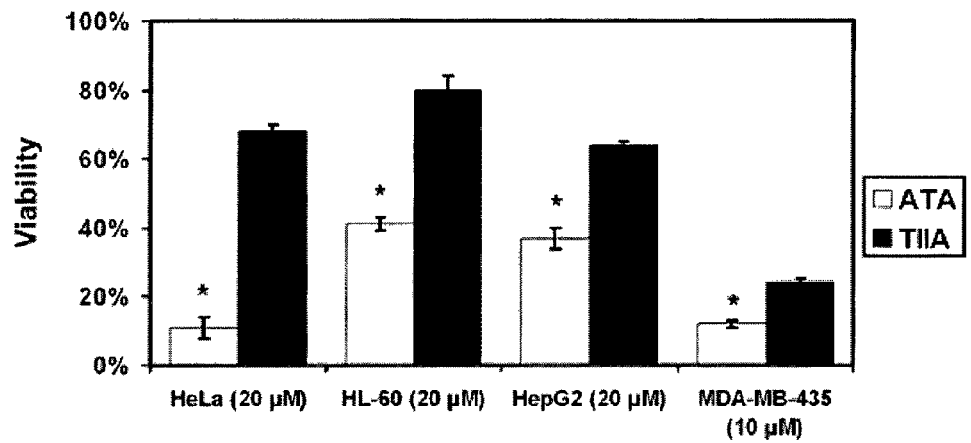
FIG. 12 shows that ATA is more potent than TIIA in causing cancer cell death. Four types of cancer cells were treated with ATA or TIIA at either 10 μM or 20 μM and the cell viability was measured by MTT assay after 48 h of compound addition. * p<0.01.

Moreover, when comparing the effects of ATA in inhibiting cell growth between cancer and non-cancer cells, it was found that the $IC_{50}$ of ATA on breast cancer SK-BR-3 cells, which overexpress HER2/c-erb-2 gene product, was much lower at 0.29 μM, while the $IC_{50}$ of ATA against MCF-10A cells derived from normal breast tissues was significantly higher at 6.64 μM. This result indicates that ATA is more potent in killing cancer cells than non-cancer cells. In addition, ATA exhibited stronger growth inhibition effect than TIIA against multiple cancer cells (FIG. 12).

Example 2

Inhibition of Tumor Growth in Nude Mice by ATA

Figure 13:
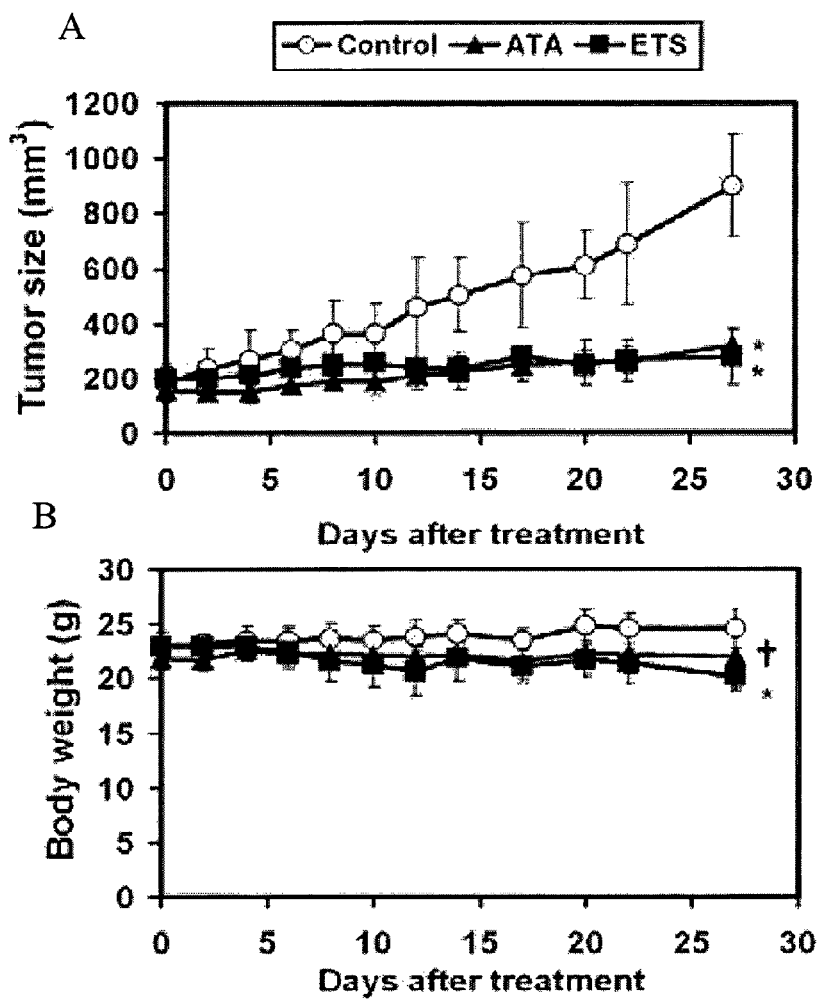
FIG. 13 shows that ATA inhibited the growth of xenografted tumors derived from human melanoma MDA-MB-435 cells in nude mice. ATA (▲ 30 mg/kg), etoposide (■ ETS, 20 mg/kg) and vehicle control (○) were injected into mice 3×/week via intraperitoneal injection. Average tumor size (A) and mice body weight (B) were measured from five mice.
Figure 14:
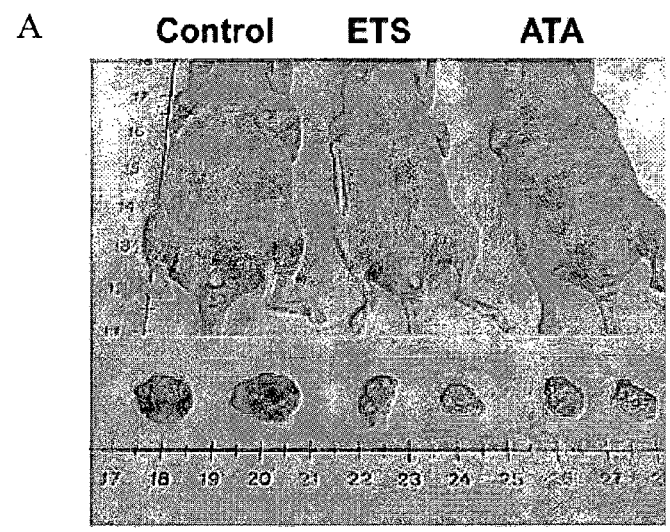
FIG. 14 shows that ATA inhibited the growth of xenografted tumors derived from human melanoma MDA-MB-435 cells in nude mice with H&E staining revealed tumor tissues morphology (A and B).
Figure 14:
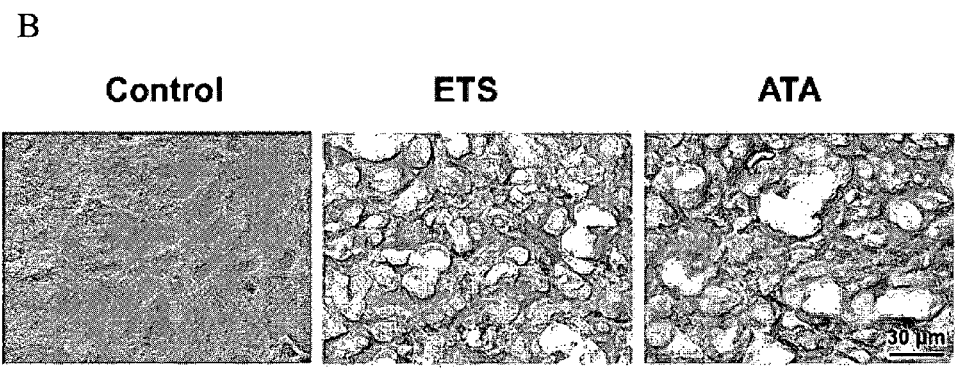

The anti-tumour effect of ATA was examined in nude mice (FIG. 13 and FIG. 14) carrying solid tumours generated by injecting human melanoma MDA-MB-435 cells into the mice subcutaneously. The tumour size and mouse body weight were monitored over a period of four weeks. Over this period significant inhibition on tumour growth was observed in the ATA-injected mice. Furthermore, the average body weight of ATA-injected mice did not significantly decrease over the control mice suggesting ATA has no significant toxicity to the animal. This result suggests that ATA can effectively kill cancer cells within a solid tumor.

Example 3

Effect of ATA on Breast Cancer Cells with High Level of HER2

Figure 15:
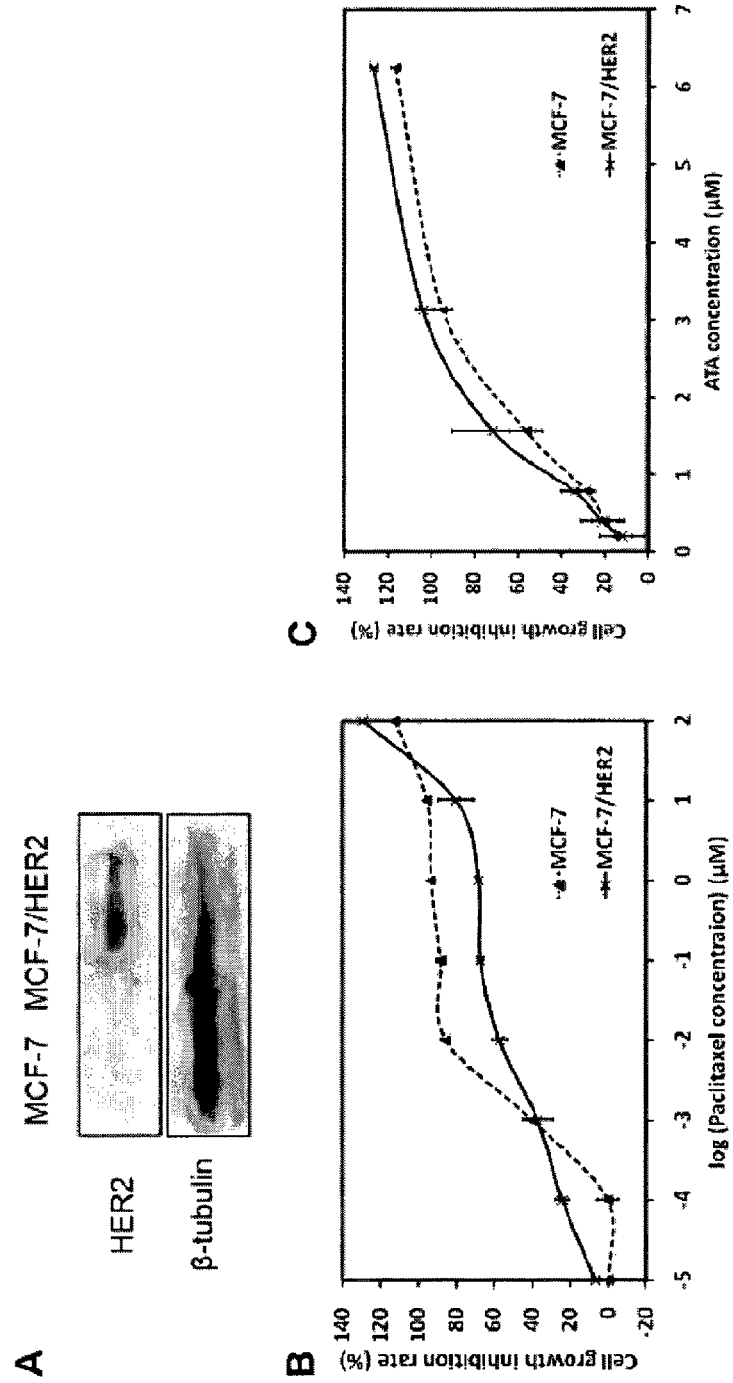
FIG. 15 shows that paclitaxel in the concentration range of $1 \times 10^{-3}$ μM to 10 μM had a much higher growth inhibition rate against HER2 negative MCF-7 cells than HER2 overexpressing MCF-7/HER2 cells, which indicates that these cells are more resistant to paclitaxel than MCF-7 cells (A and B). In contrast to their resistance to paclitaxel, MCF-7/HER2 cells displayed slightly higher sensitivity to ATA (C).

The efficacy of ATA on MCF-7 cells with over-expressed HER2 protein was investigated. It was shown (FIG. 15) that within the concentration ranges of $1 \times 10^{-3}$ μM to 10 μM, paclitaxel had a much higher growth inhibition rate against HER2 negative MCF-7 cells than MCF-7/HER2 cells, which indicates that these MCF-7/HER2 cells are more resistance to paclitaxel than MCF-7 cells. In contrast to the observed resistance of MCF-7/HER2 cells to paclitaxel, MCF-7/HER2 cells displayed higher sensitivity to ATA. In detail, ATA at the concentration range of 0.78 μM to 6.25 μM produced higher growth inhibition effects against HER2 positive MCF-7 cells than HER2 negative MCF-7 cells. Moreover, also the $IC_{50}$ of ATA at 72 h was calculated for both cell lines and the data showed that the $IC_{50}$ value for MCF-7 cells was 1.48±0.24 μM, which is significantly higher than the $IC_{50}$ value (1.0±0.23 μM) for MCF-7/HER2 cells (p=0.019). This finding suggests that ATA is more effective in inhibiting the growth of breast cancer cells over-expressing HER2 protein.

Example 4

ATA in Combination with Paclitaxel

Figure 16:
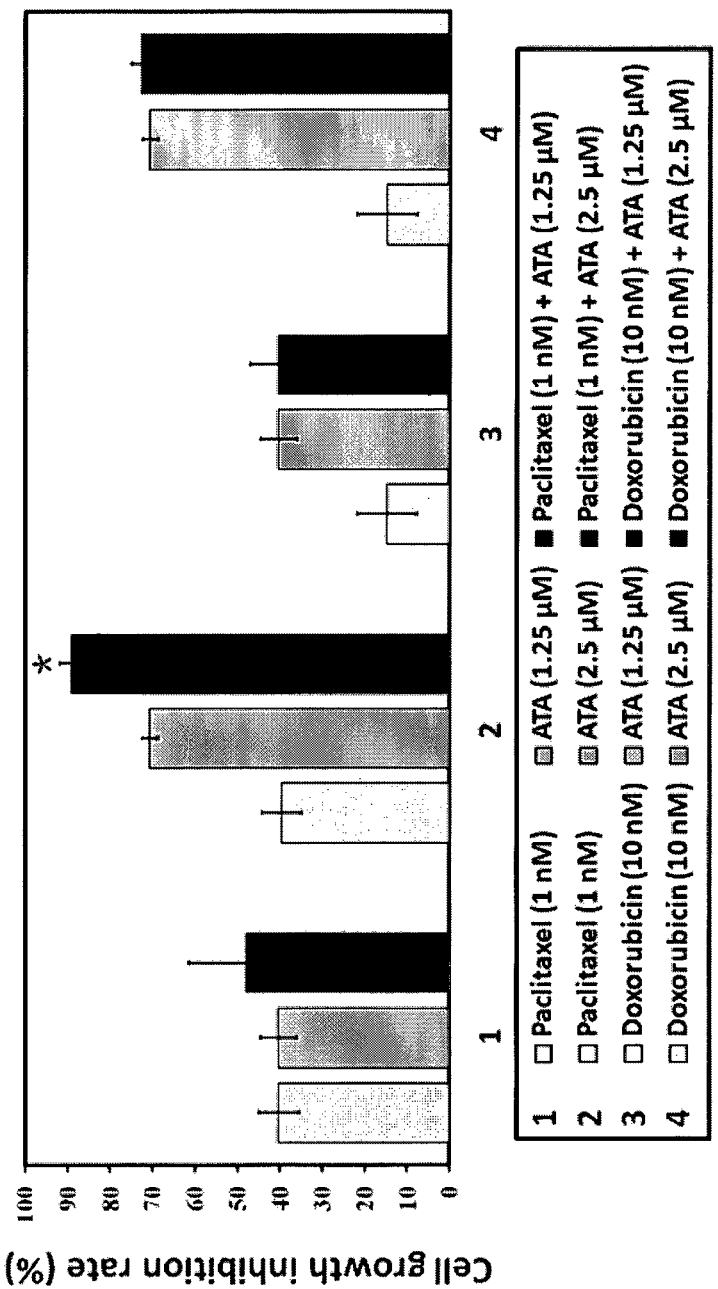
FIG. 16 shows that the combinatorial effect of ATA with either paclitaxel or doxorubicin. The effect was determined by measuring the rates of cell growth inhibition using MTT assay. (* $p<0.01$, compared with cells treated with either paclitaxel alone or ATA alone).

The inventors of the present invention have shown for the first time that ATA can increase the cytotoxic effect of paclitaxel. In the tests (FIG. 16) with five concentrations of ATA at 10, 5, 2.5, 1.25, 0.625 µM and five concentrations of paclitaxel at 1000, 100, 10, 1, 0.1 nM were used. The measured cell growth inhibition rate showed that when paclitaxel acted alone at 1 nM, it only inhibited ~40% growth of MCF-7 cells. However, when paclitaxel was used in combination with 2.5 µM ATA, the two drugs together inhibited about 89% of the cell growth, which is significantly higher than the 71% growth inhibition rate achieved by ATA alone at 2.5 µM.

Example 5

ATA can Activate the Apoptotic Pathway in Cancer Cells

Figure 17:
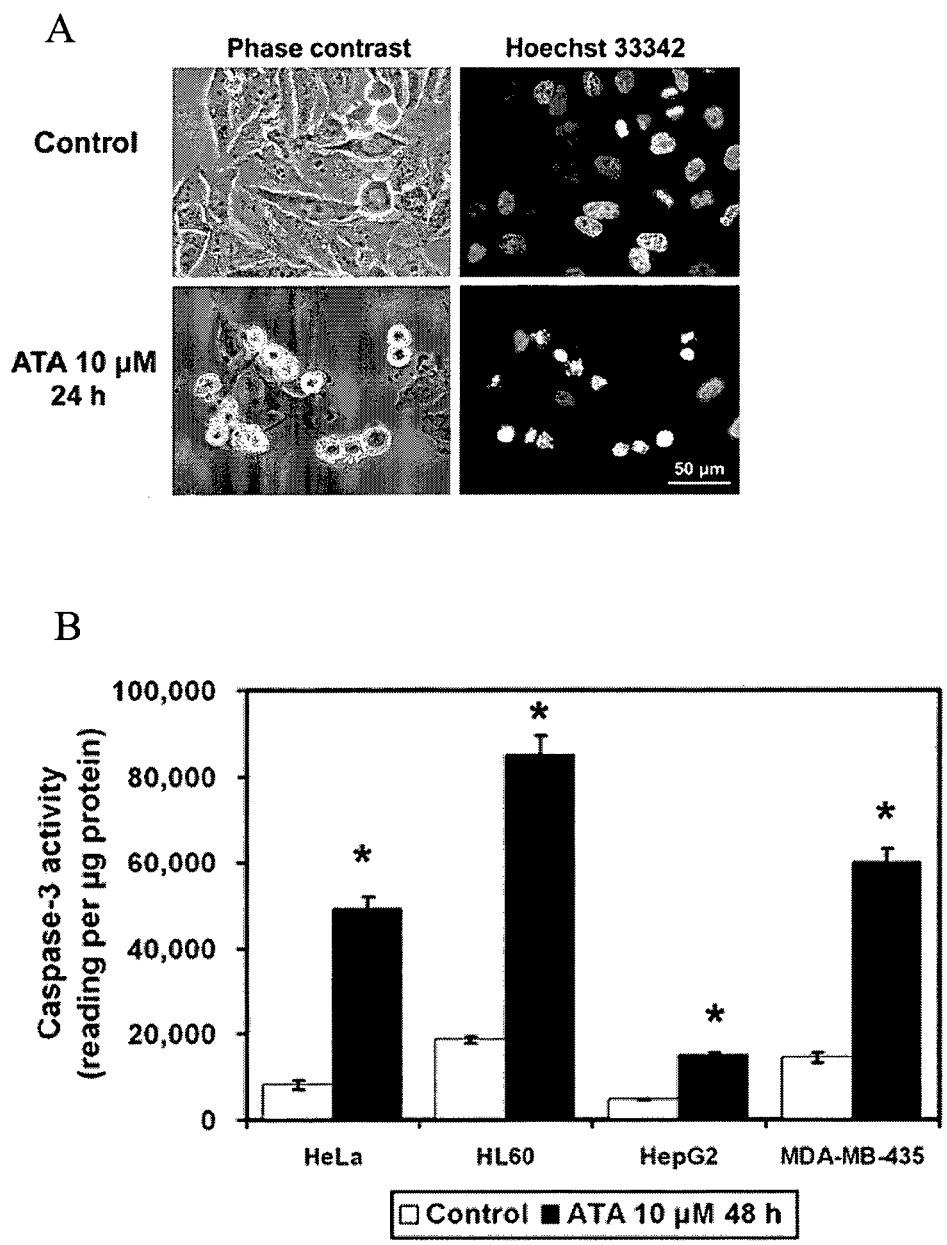
FIG. 17 shows ATA induced caspase-dependent apoptosis in cancer cells. (A) Nuclear chromosome condensation and fragmentation were observed after ATA treatment. HeLa cells were treated with 10 μM ATA for 24 h. The nuclear chromatin was stained with a DNA dye, Hoechst 33342. Scale bar=50 μm. (B) Caspase-3 activity increased after ATA treatment. Four types of cancer cells were treated with or without 10 μM ATA for 48 h and their caspase-3 activities were measured using in vitro caspase-3 activity assay. (* $p<0.01$).
Figure 18:
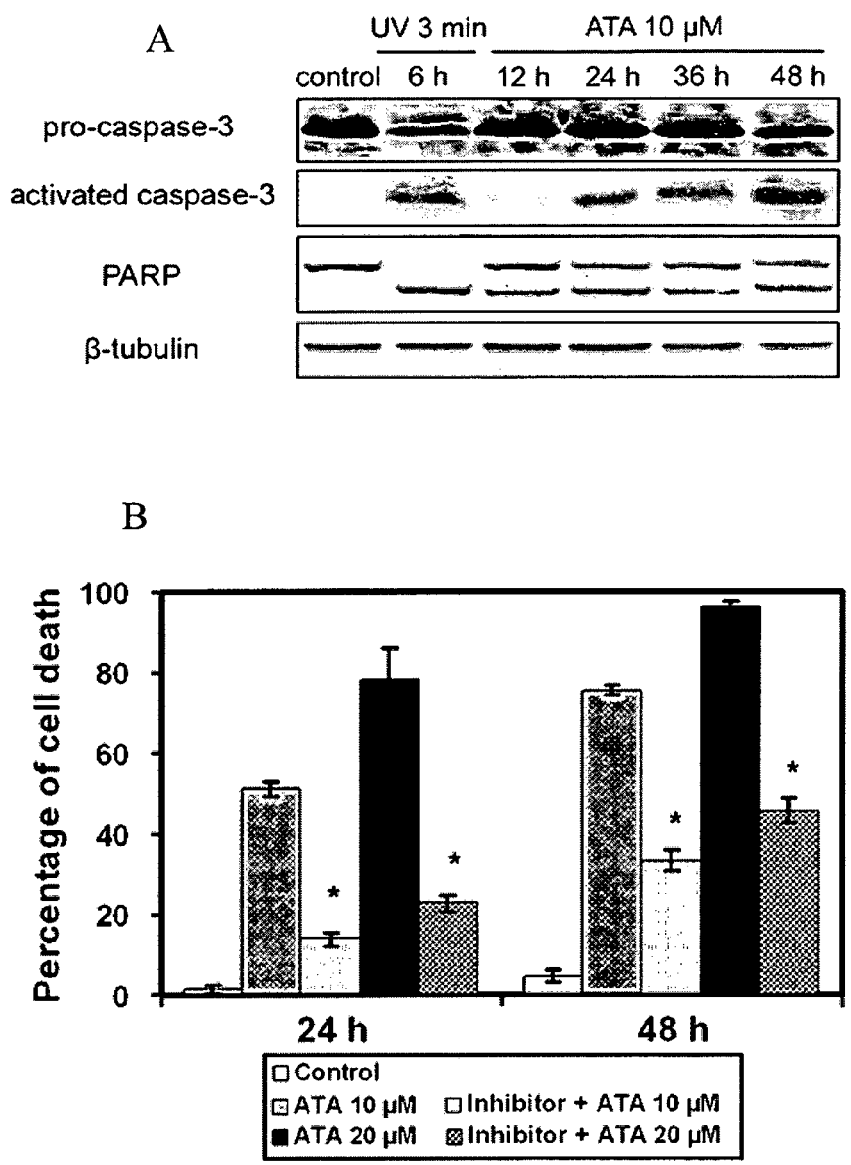
FIG. 18 shows ATA induced caspase-dependent apoptosis in cancer cells (A) Caspase-3 activation and PARP cleavage were observed after ATA treatment by Western blot analysis. HeLa cells were treated with 10 μM ATA for 12, 24, 36, and 48 h. The β-tubulin protein was probed as a loading control. (B) Pan-caspase inhibitor prevented ATA-induced cell death. HeLa cells were pre-treated with 2 μM pan-caspase inhibitor (z-VAD-fmk) for 2 h before ATA addition. Then 10 μM or 20 μM ATA were added. After 24 h and 48 h treatment, the number of died cells was counted under a microscope. (* $p<0.01$, compared with cells treated with ATA only). Control: cells without any treatment.

The inventors of the present invention have shown for the first time that ATA can activate the apoptotic pathway in cancer cells. After finding that ATA could induce caspase-related cell death in HeLa-C3 cells during primary analysis, its apoptotic ability in HeLa cells using other apoptotic assays was tested. Using Hoechst 33342 staining (FIG. 17), nuclear chromosomal condensation and fragmentation was revealed in cells treated with 10 µM ATA for 24 h. The in vitro caspase-3 activity assay results showed that the levels of caspase-3 activity increased 3.1 to 5.6 fold over the control samples after ATA treatment in four different types of cancer cells derived from cervical cancer, liver cancer, melanoma and leukemia. The activation of caspase-3 after ATA treatment was further validated by Western blot analysis, which clearly showed the formation of the activated caspase-3, and the cleavage of a caspase-3 substrate protein, PARP, into its smaller fragment (FIG. 18). Finally, it was found that the ATA-induced cell death could be inhibited by treating cells with 2 µM pan-caspase inhibitor z-VAD-fmk. Since the chromatin condensation, DNA fragmentation and caspase-3 activation have been considered as signature events occurred during apoptotic cell death, it was concluded that ATA can kill cancer cells by inducing apoptosis.

Example 6

ATA can Activated the Bax-Mediated Apoptotic Pathway

It was subsequently found that ATA can activate the Bax-mediated, mitochondria-dependent apoptotic pathway. It is well known that apoptosis can be activated mainly through two pathways: the death receptor pathway (extrinsic pathway), or the mitochondria-dependent pathway (intrinsic pathway). Both pathways can converge to mitochondria to promote the release of apoptotic factors such as cytochrome c, Smac, AIF, EndoG and HtrA2/Omi, which can activate downstream targets to trigger cell death (X. Wang, The expanding role of mitochondria in apoptosis. Genes & Development 15 (2001) 2922-293).

Figure 19:
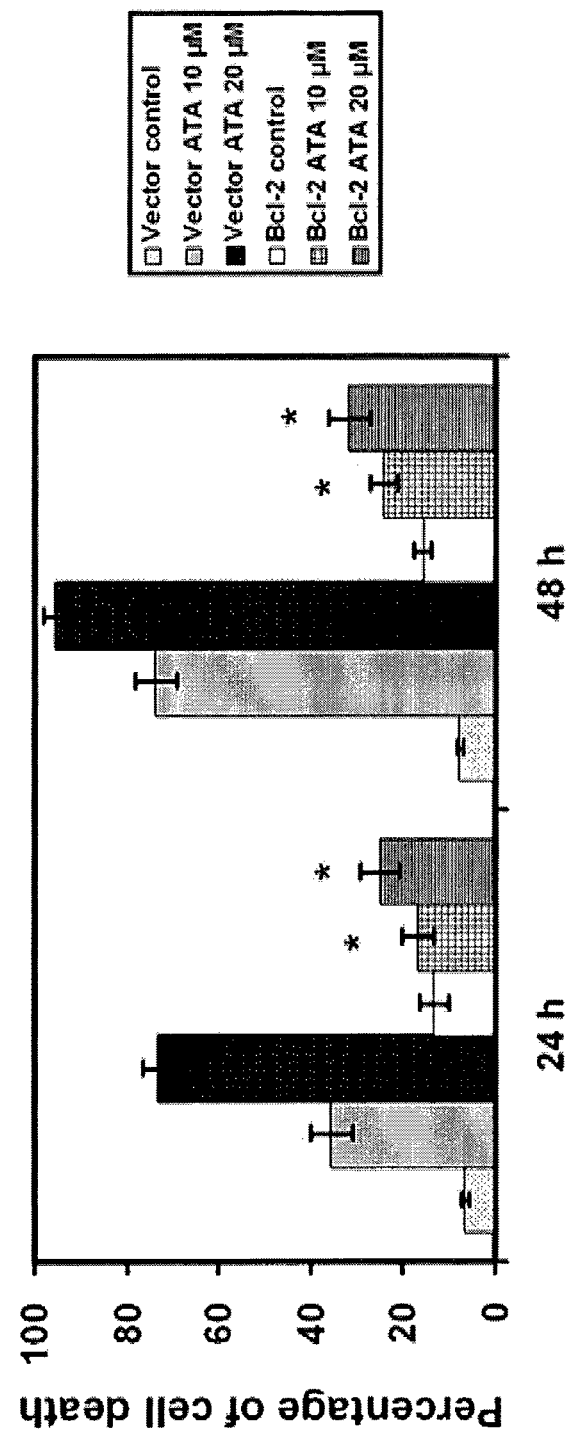
FIG. 19 shows that ATA induced apoptotic cell death via a mitochondria-dependent pathway. Overexpression of Bcl-2 inhibited ATA-induced cell death. HeLa cells transfected with either yellow fluorescent protein (YFP) (vector control) or YFP-Bcl-2 (Bcl-2) were treated with ATA at 10 or 20 μM. The percentage of cell death from YFP-positive cells was determined by cell counting under a fluorescence microscope. (* $p<0.01$, compared with vector control groups).

To distinguish which pathway is mainly used by ATA to activate apoptosis, it was examined whether the overexpression of Bcl-2, an anti-apoptotic protein that is capable of blocking mitochondria-dependent apoptosis, can significantly inhibit ATA-induced cell death. HeLa cells transfected with YFP-Bcl-2 or YFP only were treated with 10 µM or 20 µM ATA. After 24 h or 48 h treatment, the percentage of cell death in each sample was calculated by counting the numbers of fluorescence-positive cells either live (attached with a normal cell morphology) or dead (detached with a shrunk morphology) under a fluorescence microscope. Under ATA treatment, the percentage of cell death from Bcl-2 over expressing cells was significantly lower than the cells with normal Bcl-2 level (FIG. 19). This apparent protective effect of Bcl-2 on ATA-induced cell death supports the notion that ATA can induce apoptosis via a mitochondria-dependent pathway.

Figure 20:
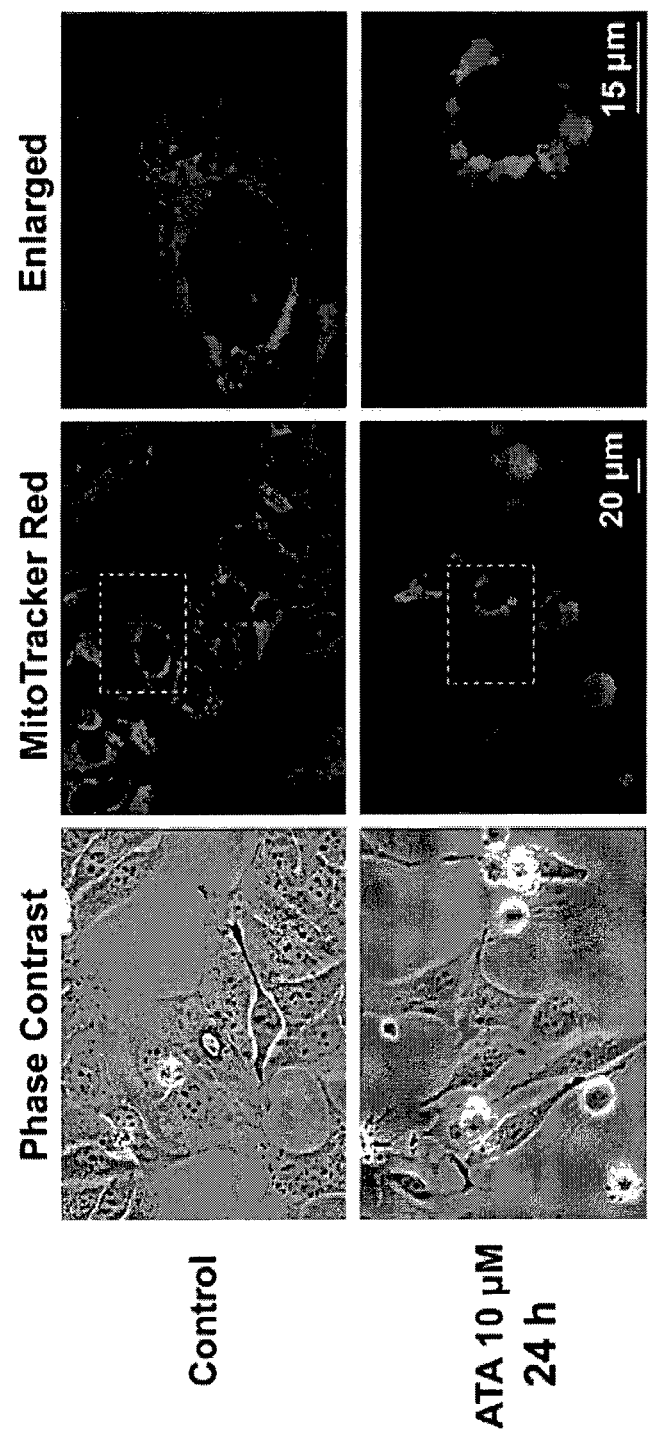
FIG. 20 shows that ATA treatment induces mitochondria swelling and membrane potential loss. HeLa cells were treated with 10 μM ATA for 24 h. Then 0.1 μM fluorescent dye MitoTracker Red was applied to the cells to reveal the mitochondria morphology and membrane potential.

Next it was examined whether ATA can activate apoptosis by causing mitochondrial damage to release those pro-apoptotic factors. To test this, mitochondria morphology changes after ATA treatment using a mitochondria-selective dye MitoTracker Red in HeLa cells were observed. It was found that after ATA treatment, some mitochondria changed their filamentous staining pattern to form aggregates; and some lost their red fluorescence, implying that mitochondria were damaged (FIG. 20). It was then investigated whether Bax is involved in ATA-related mitochondrial damage. It is well reported that during mitochondria-dependent apoptosis, Bax can translocate from cytosol to mitochondrion and form pores to permeabilize the outer membrane of mitochondrion, causing the release of cytochrome c. Cytochrome c will then bind to Apaf-1 to activate pro-caspase-9 in the presence of dATP, leading to caspase-3 activation and apoptotic cell death (D. M. Finucane, E. Bossy-Wetzel, N. J. Waterhouse, T. G. Cotter, D. R. Green, Bax-induced caspase activation and apoptosis via cytochrome c release from mitochondria is inhibitable by Bcl-xL. J Biol Chem 274 (1999) 2225-2233).

Figure 21:
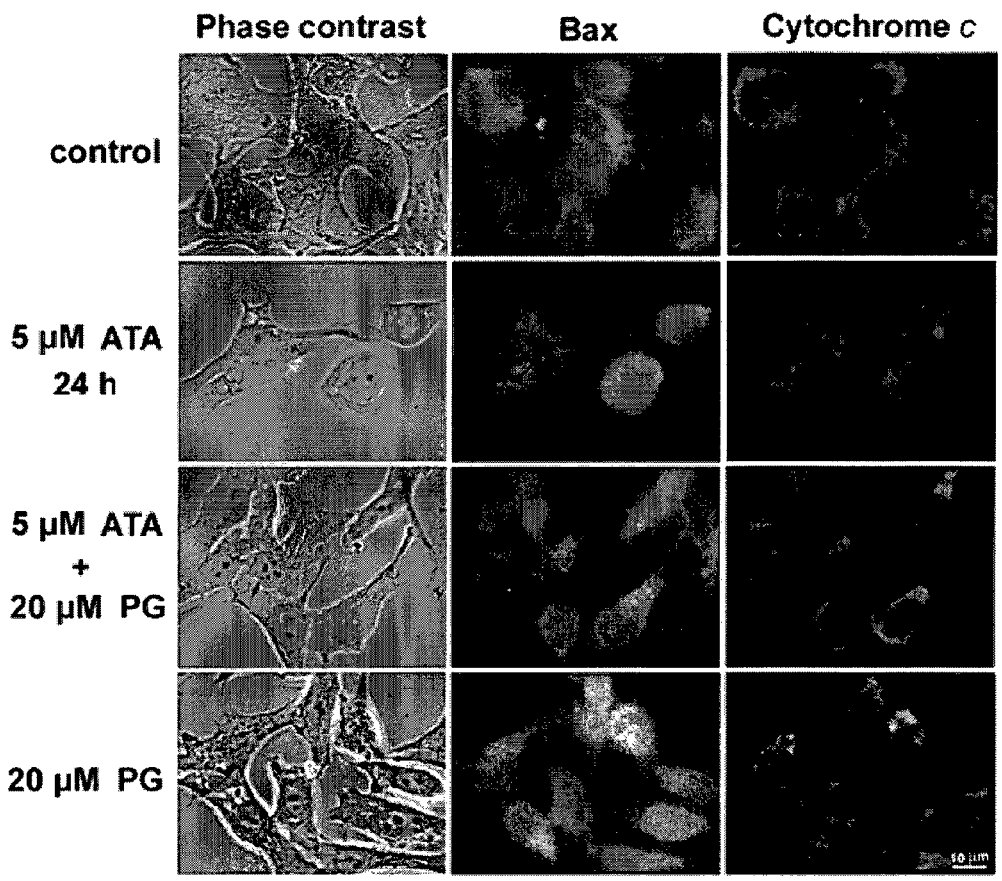
FIG. 21 shows that ATA triggered Bax translocation and cytochrome c release during apoptosis in MDA-MB-435 cells by immunofluorescence staining. An antioxidant agent, propyl gallate (PG) prevented these events. The concentration of ATA and PG were 5 μM and 20 μM, respectively. The treatment duration was 24 h. Scale bar=10 μm.
Figure 22:
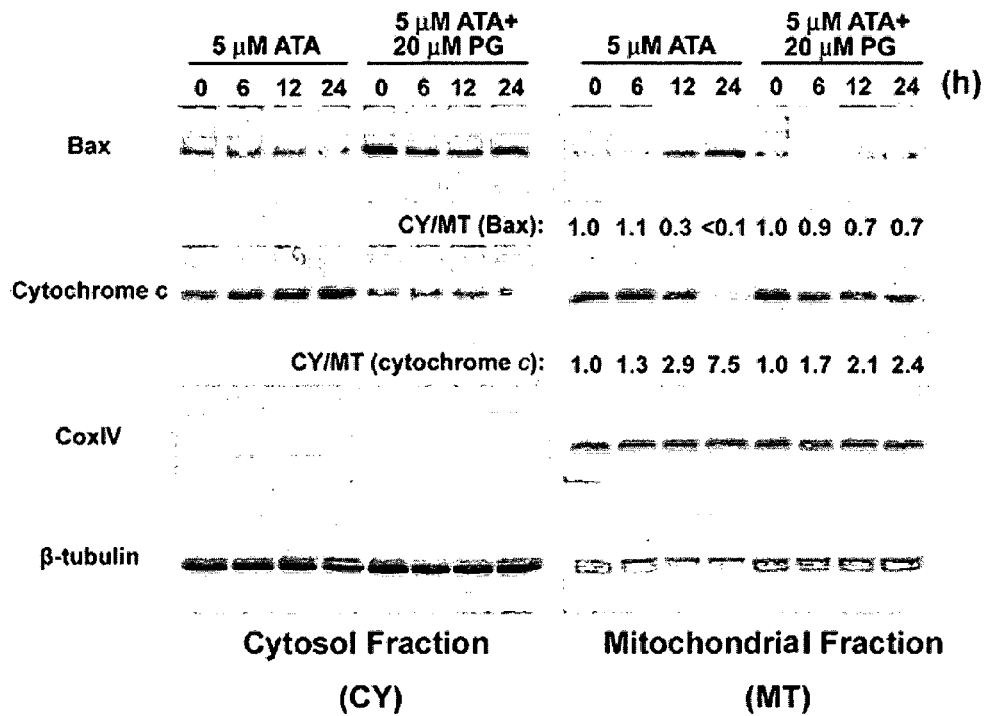
FIG. 22 shows that Bax translocation and cytochrome c release in MDA-MB-435 cells after ATA treatment by Western blot analysis. The value of CY/MT represents the ratio of integrated band intensity of cytosol fraction (CY) over corresponding integrated band intensity of mitochondrial fraction (MT). The ratio was normalized by the control group. Two proteins were used as internal markers to judge the quality of cell fractionation experiment: Cox IV for mitochondria and β-tubulin mainly for cytosol.
Figure 23:
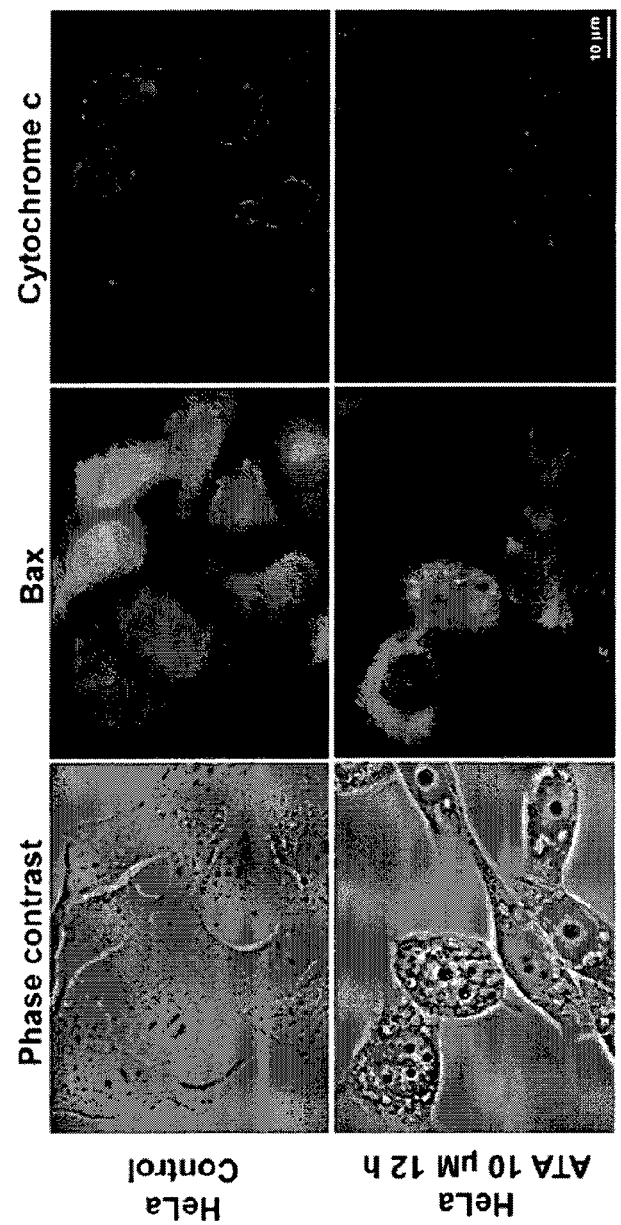
FIG. 23 shows that ATA induced Bax translocation and cytochrome c release in HeLa cells by using immunostaining.
Figure 24:
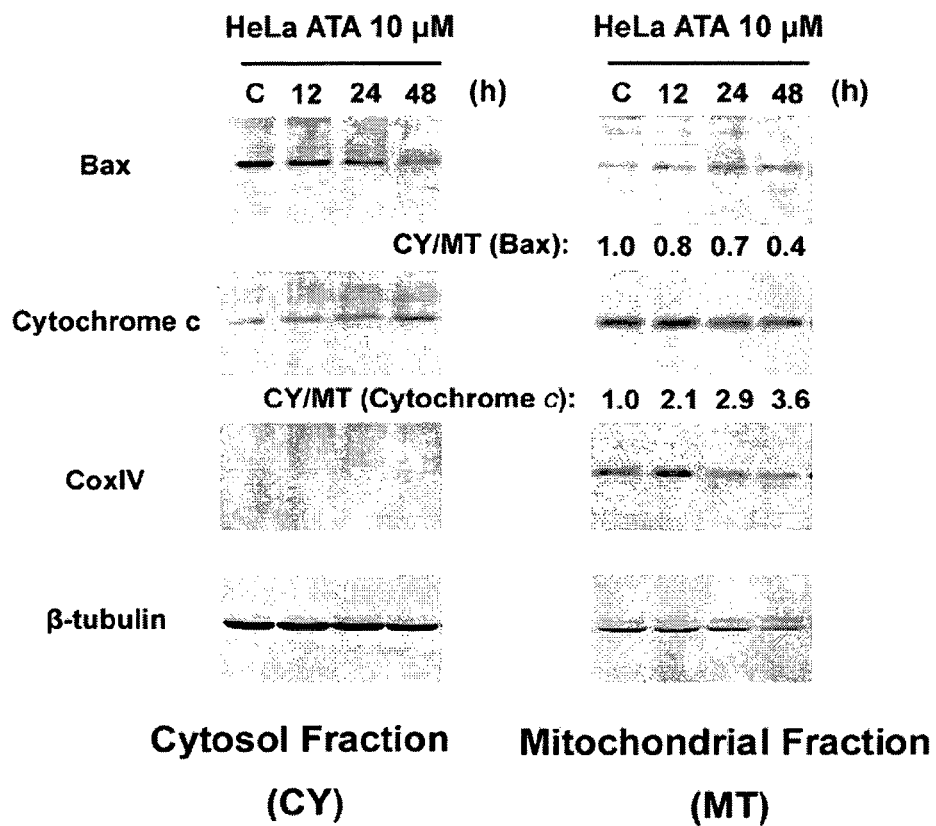
FIG. 24 shows that ATA-induced apoptosis is triggered by Bax translocation and cytochrome c release in HeLa cells. In this Western blot experiment, 10 μM ATA was used. The number (h) indicates the treatment duration in hours. The value of CY/MT represents the ratio of integrated band intensity of cytosol fraction over corresponding integrated band intensity of mitochondrial fraction. The ratio was normalized by the control group. Two proteins were used as markers to judge the quality of cell fractionation experiment: Cox IV for mitochondria and beta-tubulin mainly for cytosol.

The subcellular localization changes of Bax and cytochrome c during ATA-induced apoptosis were first examined using immunofluorescence staining. This revealed that after treating MDA-MB-435 cells with 5 µM ATA for 24 h, Bax was observed to translocate from cytosol to mitochondria to form aggregates; meanwhile, cytochrome c was released from mitochondria to cytosol to produce a diffused staining pattern (FIG. 21). Then cell fractionation-based Western blot analysis was used to confirm this finding (FIG. 22). The results showed that the level of Bax was reduced in the cytosol fraction but had increased in the mitochondrial part from the MDA-MB-435 cells treated with 5 µM ATA for 24 h. The ratio of Bax level in the cytosol to that in the mitochondria decreased from 1.0 to <0.1 at 24 h. The reverse phenomenon was observed for cytochrome c, in that its level in the mitochondrial fraction decreased, but the level in the cytosol increased. The ratio of cytochrome c level in cytosol to that in mitochondria increased from 1.0 to 7.5 at 24 h after ATA treatment. The same phenomena were also observed in HeLa cells treated with ATA (FIG. 23 and FIG. 24). These results indicate that ATA can induce apoptosis via a Bax-mediated mitochondria-dependent pathway involving its downstream target, cytochrome c.

Example 7

ATA Induces ROS Generation

Figure 25:
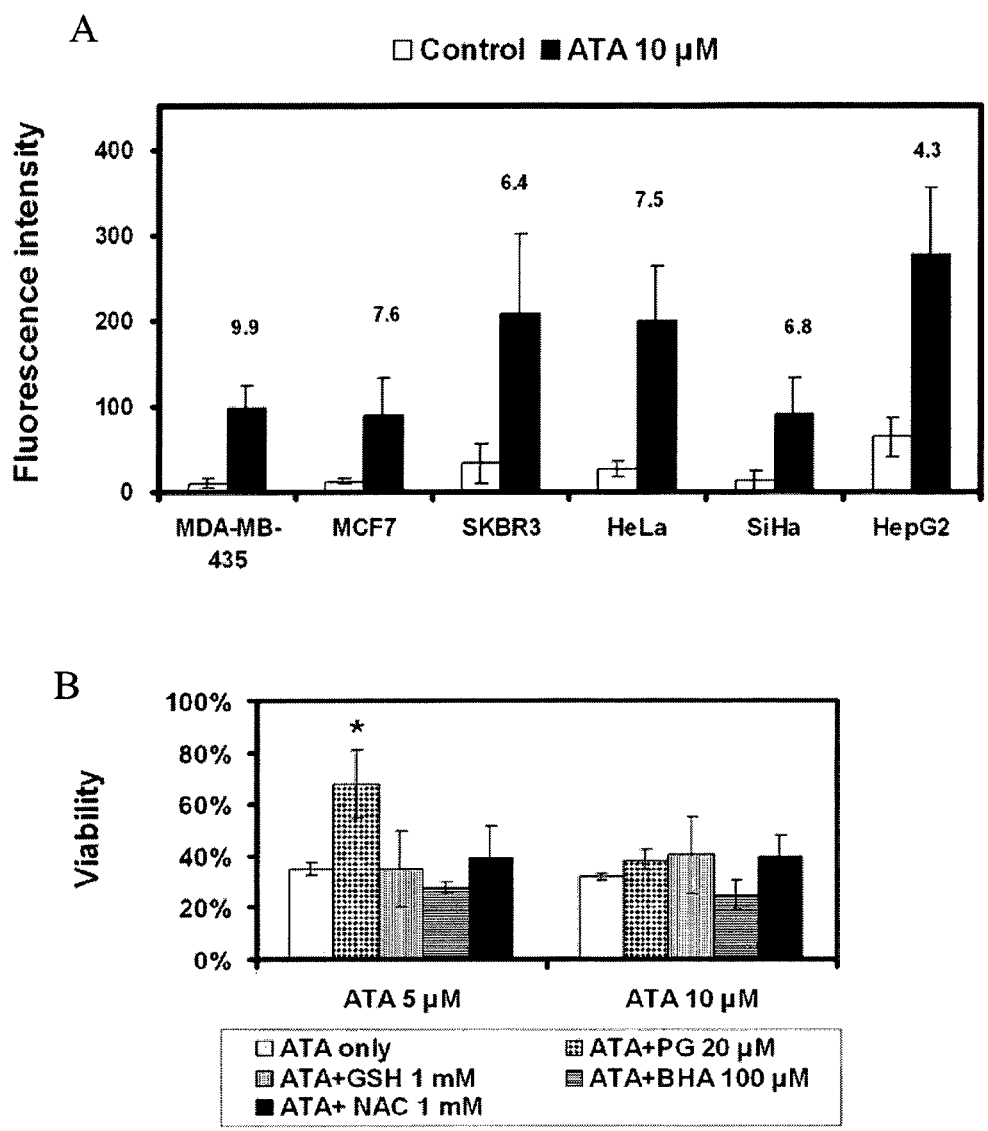
FIG. 25 shows that ATA-related ROS generation resulted in cancer cell death. (A) ROS generation in various cancer cell lines was detected using $H_2DCFDA$ after 10 μM ATA treatment for 2 h. The number indicates the fold of increase in ROS level compared to control. (B) Antioxidant prevented ATA-induced MDA-MB-435 cell death. Various antioxidants at the indicated concentration were tested for their protective effects against ATA-induced MDA-MB-435 cell death. Cells were first pre-treated with each antioxidant for 1 h and then ATA was added into the culture medium in the presence of antioxidants. The cell viability was measured by sulforhodamine B (SRB) colorimetric assay for cytotoxicity determination (* $p<0.01$).

In order to investigate how ATA triggers cell death in various cancer cells, the level of ROS in various cancer cells was measured using a fluorescent dye, $H_2DCFDA$, whose fluorescence intensity increases when the level of ROS is elevated. The results showed that various cell lines had different basal levels of ROS before ATA addition, their ROS levels were increased for 4.3 to 9.9 fold after the ATA treatment (FIG. 25A).

Since the generation of ROS was detected in all six examined cell lines and it occurred only 2 h after ATA addition, which was at least 4-6 h ahead of Bax translocation, it was speculated that ATA-mediated ROS generation might be the cause for cell death. If this assumption was correct, elimination of ROS should be able to prevent the cell death and Bax translocation after ATA addition. To test this hypothesis, MDA-MB-435 cells were pre-treated with different kinds of antioxidants including 20 μM propyl gallate (PG), 1 mM glutathione (GSH), 100 μM butylated hydroxyanisole (BHA) and 1 mM N-acetylcysteine (NAC) for 1 h. ATA was afterwards added to the cells at 5 μM and 10 μM, respectively. The percentage of cell death after 24 h of ATA treatment was measured using SRB cytotoxicity assay. The results showed that the antioxidant PG, could significantly increase the cell viability from 35% to near 68% against 5 μM ATA. Furthermore, quantitative analysis revealed that 20 μM of PG were sufficient to significantly prevent 5 μM ATA-induced cell death in MDA-MB-435 cells (FIG. 25B).

Figure 26:
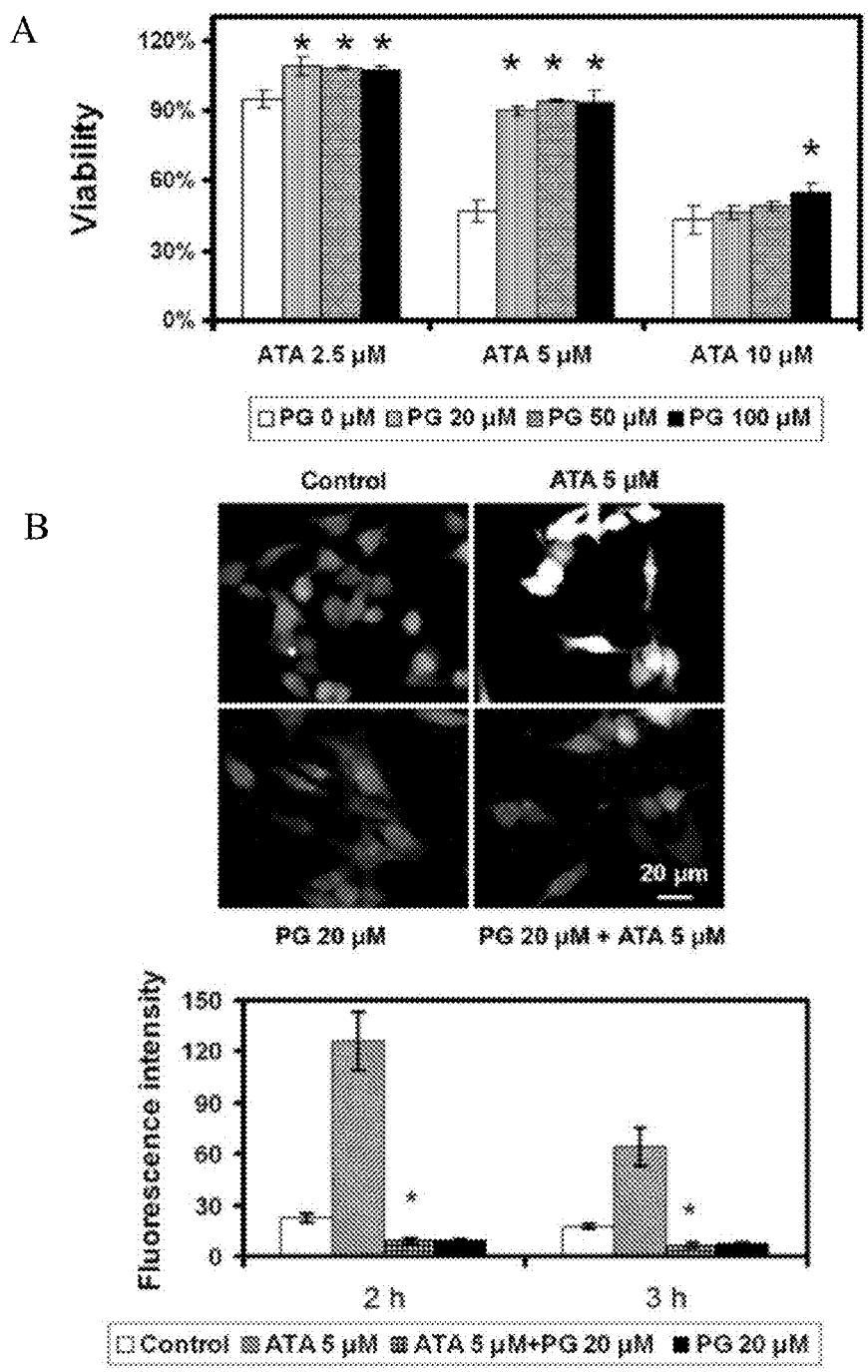
FIG. 26 shows that ATA-related ROS generation resulted in cancer cell death. (A) PG prevented ATA-induced cell death. Three concentrations of PG were tested for their protective effects on ATA-induced cell death. The cell viability was measured by SRB assay. (* $p<0.01$). (B) PG protected ROS generation caused by ATA treatment. Top panel shows the fluorescence images of MDA-MB-435 cells under different treatment conditions while bottom panel shows the average fluorescence intensity (* $p<0.01$, compared to 5 μM ATA treatment). All the experiments were performed at least three times. The results presented in this figure are the average of three experiments. Error bar represents standard deviation. Scale bar=20 μm.
Figure 27:
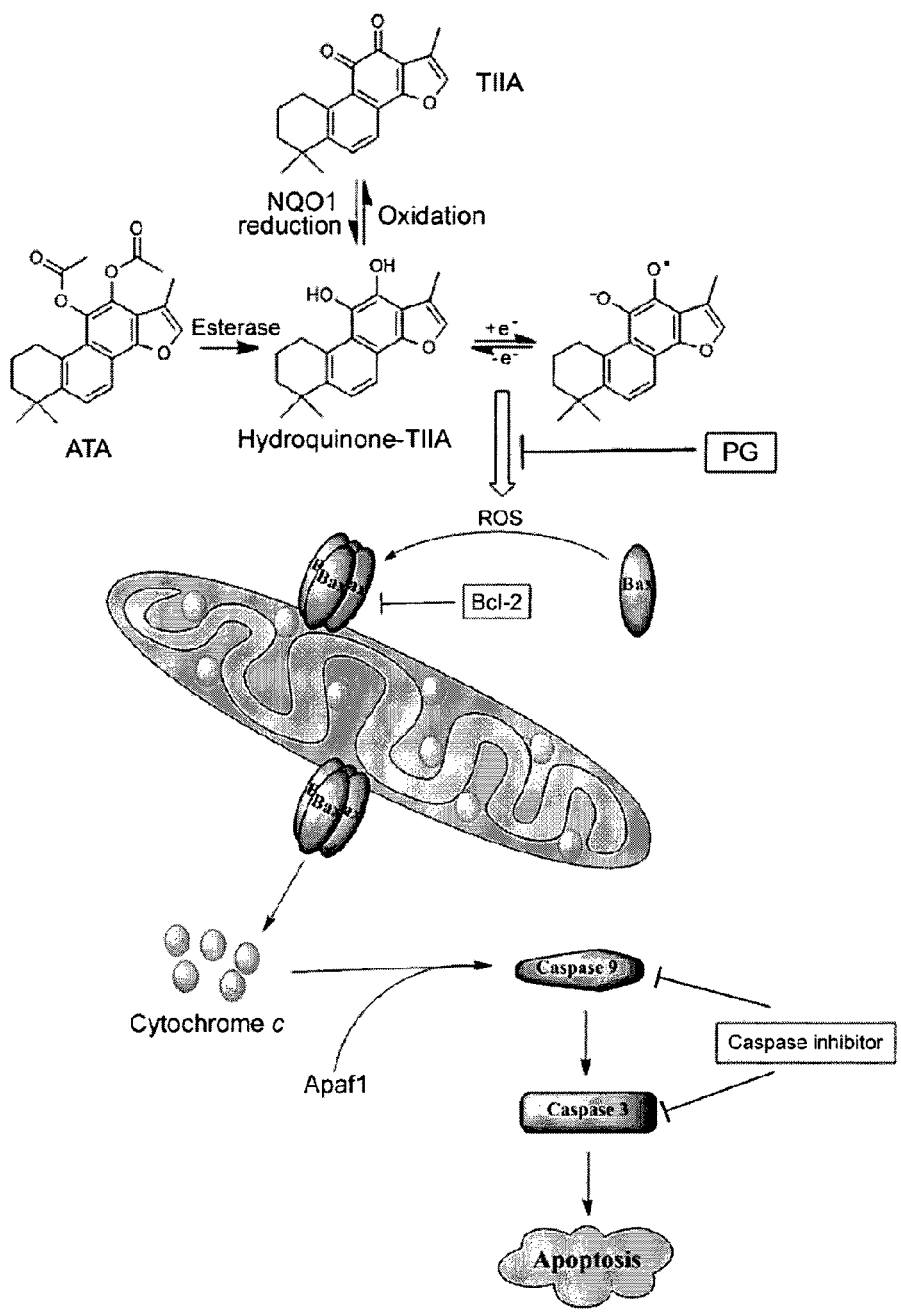
FIG. 27 schematically illustrates the mechanism of ATA in generating ROS and inducing apoptosis in cancer cells.

It was further tested, whether PG could prevent ROS generation after ATA treatment. It was found that a high level of ROS was produced in MDA-MB-435 cells after ATA addition reaching the maximum level at 2 h. And this ATA-induced ROS level increase was completely prevented by pre-treating cells with 20 μM PG (FIG. 26). Moreover, results of immunofluorescence staining (FIG. 21) and Western blot analysis (FIG. 22) showed that PG could effectively prevent Bax translocation and cytochrome c release in ATA-treated MDA-MB-435 cells. In summary, this data shows that ATA can induce Bax-mediated mitochondria-dependent apoptosis by generating reactive oxygen species (FIG. 27).

Example 8

Cytotoxicity of ATA in Cancer Cell Lines and Normal Cells

The cytotoxcitiy of ATA was assessed in cancer cell lines and normal cells. In order to do so the $IC_{50}$ of ATA at 72 h in multiple cancer cell lines or normal cell lines including muscle and fibroblast cells was evaluated. As shown in Table 2, ATA has lower $IC_{50}$ on cancer cells derived from cervical cancer, lung cancer, colon cancer, liver cancer, neuroblastoma and leukemia, but relative higher $IC_{50}$ on non-cancer cells including myoblast cells from muscle and fibroblast cells from lung tissue.

TABLE 2

$IC_{50}$ of ATA at 72 h on various cancer or non-cancer cell lines

| Cell type | Organ | $IC_{50}$ (μM) |
|---|---|---|
| HeLa | Cervical cancer cells | 0.69 ± 0.19 |
| A549 | Lung cancer cells | 0.81 ± 0.13 |
| SK-N-SH | Neuronblastoma | 1.24 ± 0.12 |
| K-562 | Leukaemia cells | 1.69 ± 0.34 |
| HCT 15 | Colorectal adenocarcinoma | 0.56 ± 0.08 |
| HCT 116 | Colorectal adenocarcinoma | 2.28 ± 0.49 |
| Caco2 | Colorectal adenocarcinoma | 2.50 ± 0.45 |
| HepG2 | Liver cancer cells | 4.27 ± 0.73 |
| C2C12 (non-cancerous) | Myoblast (normal muscle cells) | 10.15 ± 1.44 |
| IMR-90 (non-cancerous) | Fibroblast (normal lung cells) | 15.54 ± 0.71 |

Example 9

Effect of ATA on Different Breast Cancer Cells

Figure 3:
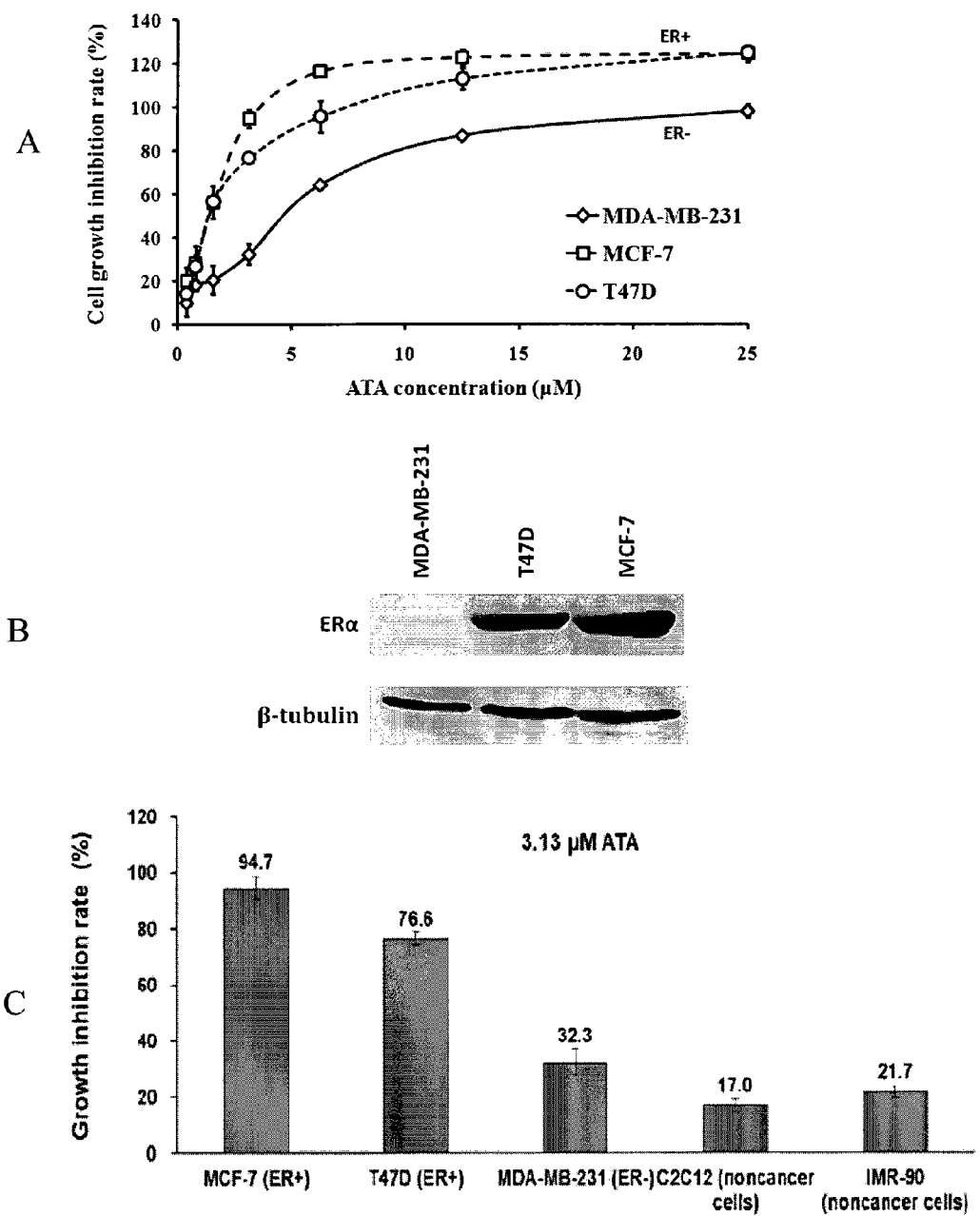
FIG. 3 shows (A) Growth inhibition rates of ATA measured from breast cancer cells of ER− MDA-MB-231, ER+/MCF-7, and ER+/T47D cells after 72 h of ATA treatment at different concentrations by MTT assay. (B) Protein level of ERα detected by Western blot analysis. (C) Growth inhibition rates measured after 72 h of 3.13 μM ATA treatment by MTT assay.

Surprisingly it was found that ATA displayed much higher growth inhibition effect on ER-positive breast cancer cells such as MCF-7 and T47D than ER-negative breast cancer cells such as MDA-MB-231 (FIG. 3). The $IC_{50}$ value of ATA at 72 h is about 5.4-5.7 fold lower between ER-positive and ER-negative cells which indicates the selective growth inhibition ability of ATA towards ER-positive breast cancer cells (Table 3).

TABLE 3

$IC_{50}$ values of ATA at 72 h on ER+ and ER− breast cancer cells

| | ER− | ER+ | | Ratio of ER−/ER+ | |
|---|---|---|---|---|---|
| | MDA-MB-231 | MCF-7 | T47D | 231/MCF-7 | 231/T47D |
| $IC_{50}$ of ATA (μM) | 7.98 ± 0.18 | 1.48 ± 0.24 | 1.40 ± 0.20 | 5.4 | 5.7 |

In addition, results in FIG. 3C also show that ATA is more specific in inhibiting the proliferation of ER+ breast cancer cells but less toxic to normal cells including muscle C2C12 and fibroblast IMR-90 cells.

Example 10

Potency of ATA Compared to Tamoxifen

Figure 4:
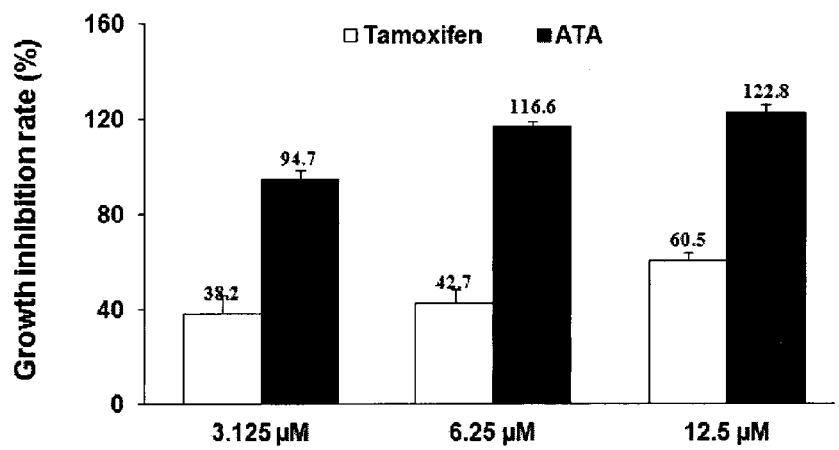
FIG. 4 shows growth inhibition rates of tamoxifen and ATA at three concentrations measured from ER+ breast cancer MCF-7 cells at 72 h by MTT assay.

Tamoxifen, an antagonist of the estrogen receptor in breast tissue via its active metabolites, 4-hydroxytamoxifen and endoxifen, is the usual endocrine (anti-estrogen) therapy for hormone receptor-positive breast cancer in pre-menopausal women, and is also a standard in post-menopausal women although aromatase inhibitors are also frequently used in that setting. Thus, in order to evaluate the potency of ATA to be used in breast cancer therapy, its anticancer potency was compared with tamoxifen on ER-positive MCF-7 cells. FIG. 4 shows that ATA exhibited 57-74% higher growth inhibition rate at the three tested drug concentrations. This result was confirmed via comparing the $IC_{50}$ values between the two drugs on two ER-positive breast cancer cell lines. As demonstrated in Table 4, 6.7 fold less of ATA is needed than tamoxifen to inhibit 50% of ER-positive cell growth.

TABLE 4

IC$_{50}$ values of ATA and tamoxifen at 72 h on different breast cancer cells

| Type | Cell line | IC$_{50}$ of tamoxifen (μM) | IC$_{50}$ of ATA (μM) | IC$_{50}$ ratio of tamoxifen/ATA |
|---|---|---|---|---|
| ER− | MDA-MB-231 | 21.80 ± 2.90 | 7.98 ± 0.18 | 2.7 |
| ER+ | MCF-7 | 10.00 ± 0.20 | 1.48 ± 0.24 | 6.8 |
| ER+ | T47D | 9.40 ± 0.60 | 1.40 ± 0.20 | 6.7 |
| ER+/HER2+ | BT474 | 6.20 ± 0.10 | 1.00 ± 0.02 | 6.2 |

Example 11

The Metabolic Product of ATA

Figure 5:
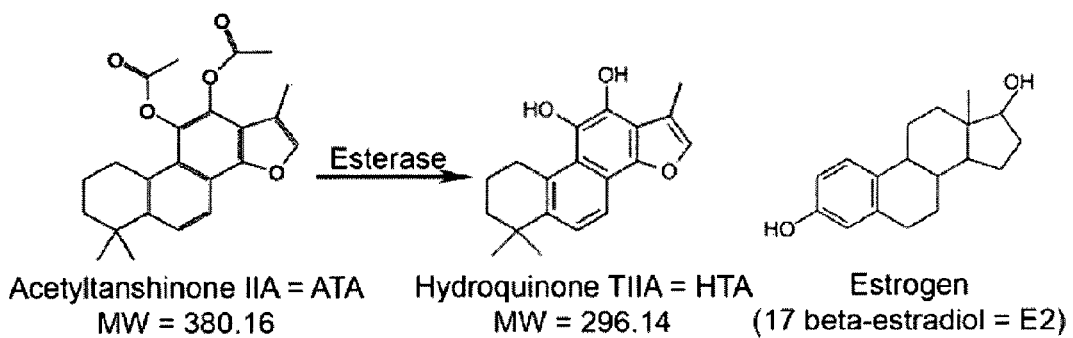
FIG. 5 depicts the structures of ATA, HTA and estrogen.

In order to find the molecular target of ATA, the metabolic product of ATA after it enters into the cells was determined. By using LC-MS analysis, the appearance of hydroquinone TIIA (HTA) within 2 h of ATA addition to MCF-7 cells was detected. One possible mechanism of HTA formation is that after ATA enters cells its acetyl groups are removed by the esterase that is abundant in the cells (FIG. 5):

Example 12

ATA can Cause ERα Degradation in Breast Cancer MCF-7 Cells

There are two different forms of the estrogen receptor, usually referred to as α and β, each encoded by a separate gene (ESR1 and ESR2, respectively). Hormone-activated estrogen receptors form dimers, and, since the two forms are coexpressed in many cell types, the receptors may form ERα (αα) or ERβ (ββ) homodimers or ERαβ (αβ) heterodimers. Estrogen receptor alpha and beta show significant overall sequence homology, and both are composed of five domains (listed from the N- to C-terminus; amino acid sequence numbers refer to human ER): (A-F domain).

Figure 6:
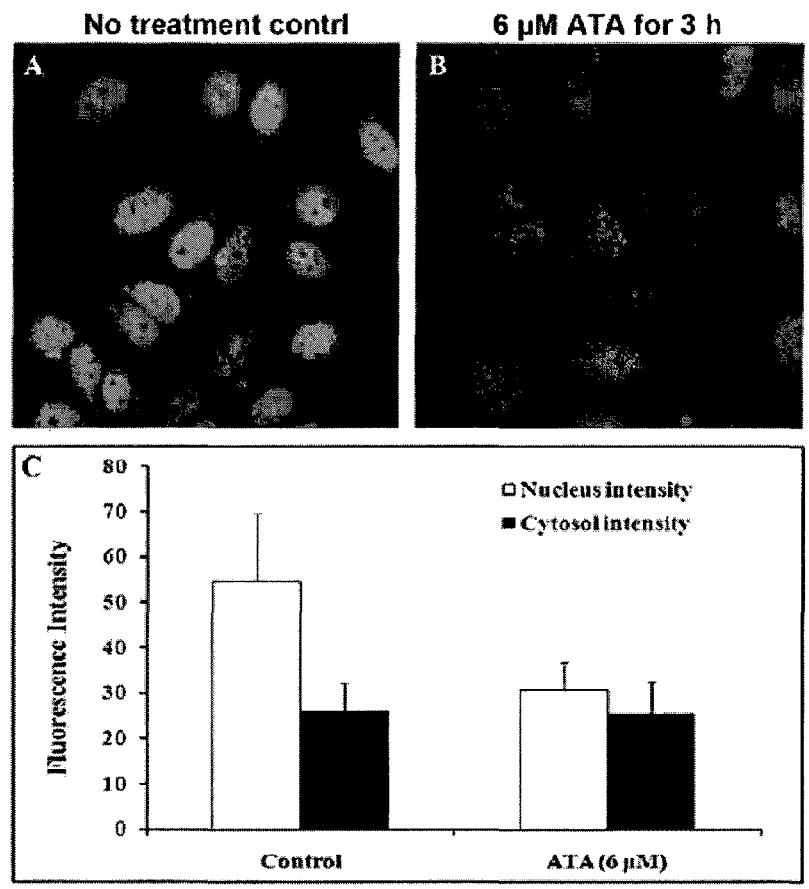
FIG. 6 shows results of quantified immunostaining of ERα in MCF-7 cells after treatment with 6 μM ATA for 3 h.

Thus, immunostaining was used to exam the protein level of ERα in MCF-7 cells after ATA treatment. It was observed that ERα was mainly localized in the nucleus (FIG. 6A) in the control cells, which had been cultured in the charcoal-stripped medium for 4 days. Three hours after 6 μM ATA treatment, the level of ERα in the nucleus was greatly reduced probably due to protein degradation (FIG. 6B). However, the fluorescence intensity in the cytosol remained unchanged after ATA treatment (FIG. 6C). This result indicates that ATA may induce the nuclear portion of ERα degradation in MCF-7 cells.

Figure 7:
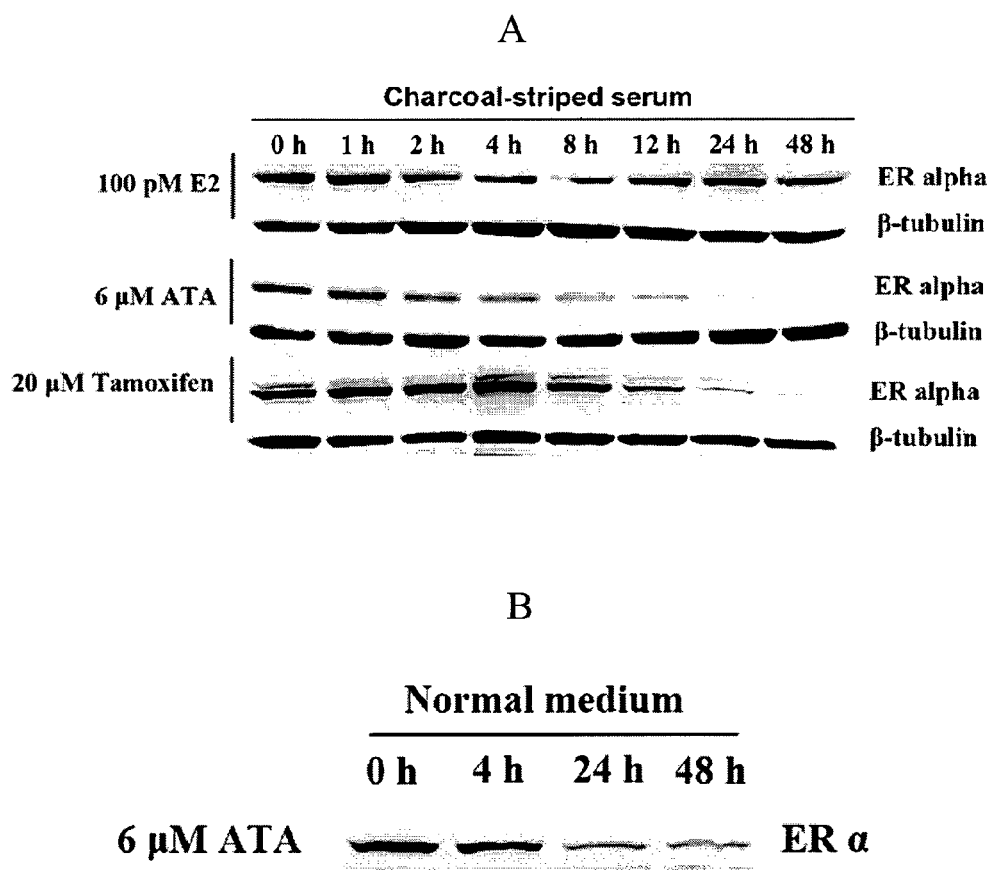
FIG. 7 shows (A) Western blot analysis of ERα levels in charcoal-stripped medium-cultured MCF-7 cells at different times with different compound treatments. (B) Western blot analysis of ERα levels in normal medium-cultured MCF-7 cells at different times with 6 μM ATA treatment.

Subsequently, Western blot analysis was used to confirm this prediction. The data in FIG. 7A shows that the total protein level of ERα was slightly reduced at 4 h and significantly reduced after 8 h of ATA treatment, which is much faster than the time for tamoxifen to induce ERα degradation. To ensure that ATA produced a similar effect in the MCF-7 cells under a physiological condition, Western blotting was used to determine the protein level of ERα in normal medium-cultured MCF-7 cells with or without ATA treatment. As shown in FIG. 7B, ATA significantly decreased the ERα protein level at 24 and 48 h in breast cancer MCF-7 cells.

Example 13

The Effect of ATA on Estrogen Receptor 1 Gene ESR1

Figure 8:
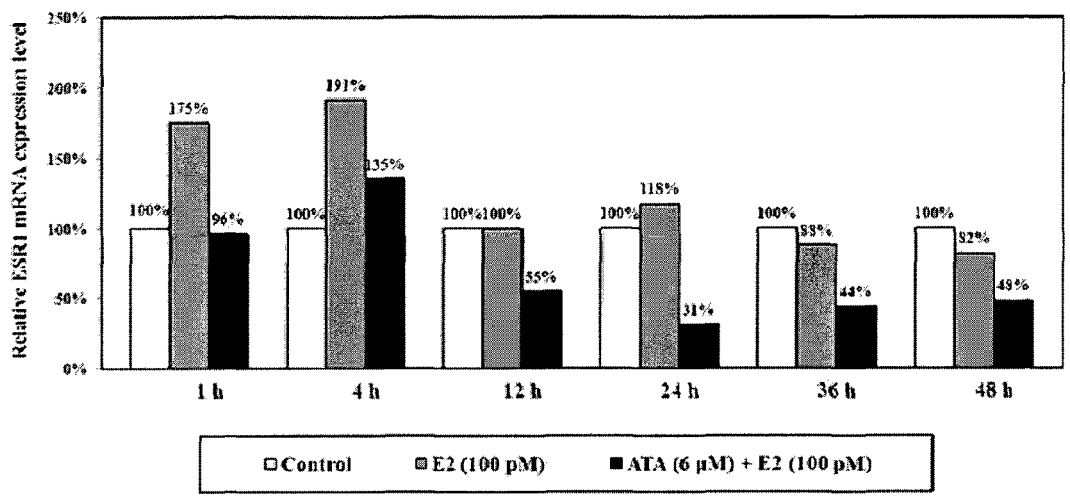
FIG. 8 shows (A) Real-time PCR analysis of relative ESR1 mRNA levels in charcoal-stripped medium-cultured MCF-7 cells at different times with 100 pM estrogen (E2) or 100 pM estrogen plus 6 μM ATA treatment. (B) Real-time PCR analysis of relative ESR1 mRNA levels in charcoal-stripped medium or normal medium-cultured MCF-7 cells at 24 h with 100 pM estrogen, 100 pM estrogen plus 6 μM ATA or 100 pM estrogen plus 6 μM tamoxifen treatment.
Figure 8:
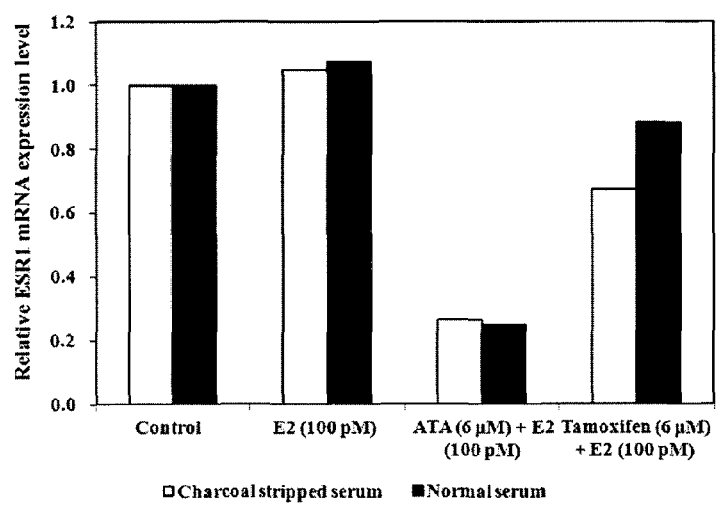

In the next step it was examined whether ATA could affect the mRNA level of ESR1 (estrogen receptor 1), which is the ERα protein encoding gene, using the method of real-time PCR. The mRNA level of a non-ERα responsive gene-GAPDH was measured and used as a reference. MCF-7 cells cultured in the charcoal-stripped medium were used as control for the 0 h sample. MCF-7 cells were treated with 100 pM estrogen (E2) or 100 pM estrogen plus 6 μM ATA for 1, 4, 12, 24, 36 and 48 h. As shown in FIG. 8A, after 12 h of 6 μM ATA treatment, the level of ESR1 mRNA reduced to 55% over control. And after 24 h of ATA treatment, the level of ESR1 mRNA further reduced to 31% over the control. This reduction effect of ATA was sustained at 36 h and 48 h and maintained the ESR1 mRNA level of ATA-treated group at about 50% over the control. Moreover, also the ability of ATA to reduce ESR1 mRNA level was compared with that of tamoxifen in normal medium-cultured MCF-7 cells. As shown in FIG. 8B, in normal medium-cultured MCF-7 cells, ATA significantly decreased ESR1 mRNA level to about 30% over the control, which is similar to the reduction level observed in MCF-7 cells cultured in a charcoal-stripped medium. However, tamoxifen only decreased the relative ESR1 level to about 70% over the control in charcoal-stripped medium cultured-MCF-7 cells. And in normal medium-cultured MCF-7 cells, tamoxifen only slightly decreased the ESR1 mRNA level compared to the control (FIG. 8B). In summary, these results show that ATA not only caused ERα protein degradation, but also reduced ESR1 mRNA expression in human breast cancer MCF-7 cells.

Example 14

Effect of ATA on the ER-Responsive Gene GREB1

As ER is a transcription factor, its degradation should directly affect the production of mRNA from ER-responsive genes. To test this prediction, real-time PCR was used to measure the mRNA level of GREB1 (growth regulation by estrogen in breast cancer 1) which is an early estrogen-responsive gene in the ER-regulatory pathway.

Figure 9:
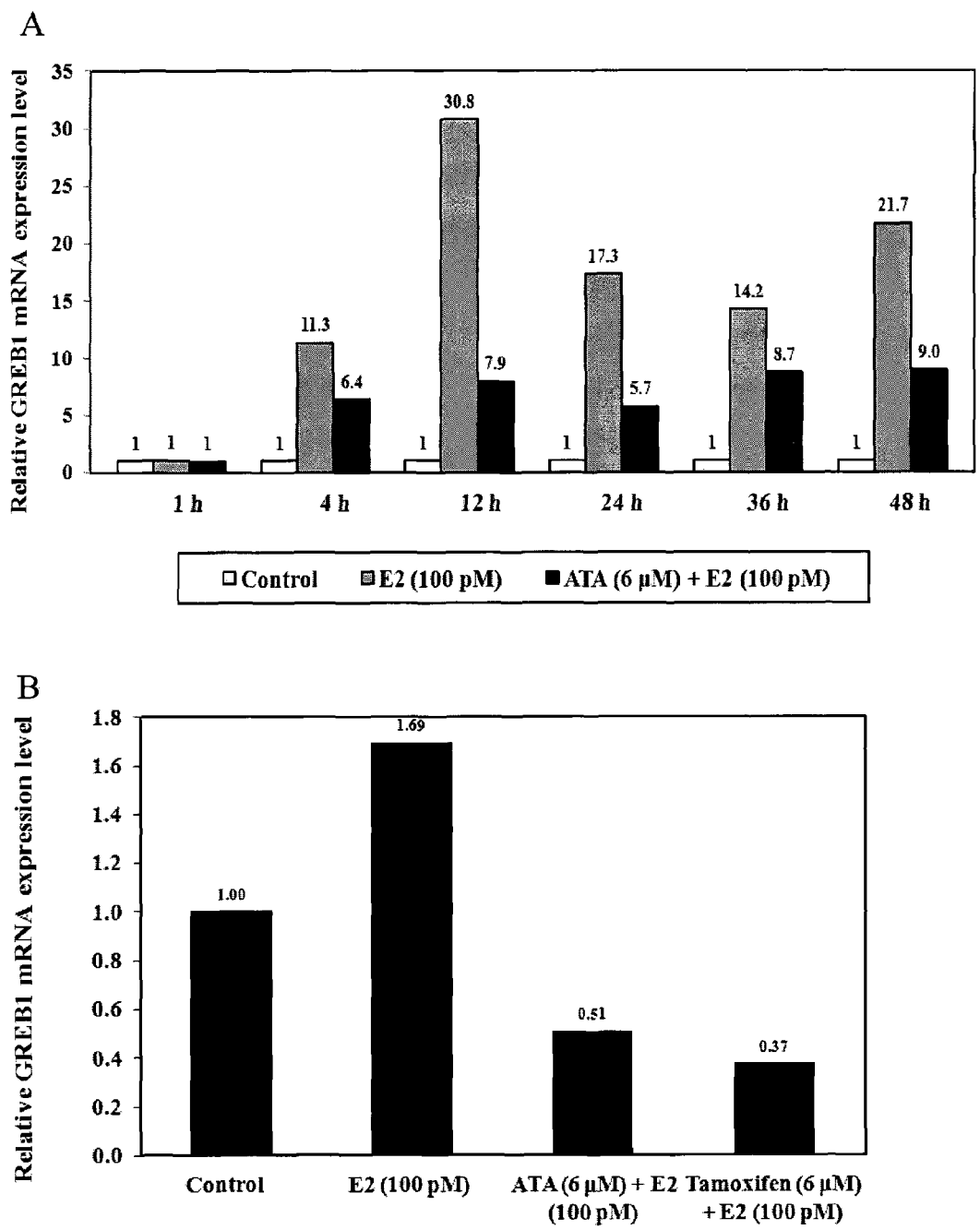
FIG. 9 shows (A) Real-time PCR analysis of relative GREB1 mRNA levels in charcoal-stripped medium-cultured MCF-7 cells at different times with 100 pM estrogen (E2) or 100 pM estrogen-plus 6 μM ATA treatment. (B) Real-time PCR analysis of relative GREB1 mRNA levels in normal medium-cultured MCF-7 cells at 24 h with 100 pM estrogen, 100 pM estrogen plus 6 μM ATA or 100 pM estrogen plus 6 μM tamoxifen treatment.

In order to do so, the mRNA level of a non-ER regulated gene GAPDH was measured and used as a reference. MCF-7 cells cultured in the charcoal-stripped medium were used as a control. MCF-7 cells were treated with 100 pM estrogen (E2) or 100 pM estrogen plus 6 μM ATA for 1, 4, 12, 24, 36 and 48 h. As shown in FIG. 9A, treating MCF-7 cells with estrogen for 4 h increased the GREB1 mRNA level for 11.3 fold of the control. However, this increase of estrogen-induced GREB1 transcription was clearly reduced to 6.4 fold by ATA treatment. A more significant reduction of the GREB1 mRNA level (from 30.8 fold to 7.9 fold) was observed after 12 h of ATA treatment. Similarly, at the following time points, ATA effectively inhibited estrogen-induced GREB1 gene transcription.

Furthermore, the effect of reducing ERα-responsive gene GREB1 expression was compared between ATA and tamoxifen in normal medium-cultured MCF-7 cells. As shown in FIG. 9B, 100 pM estrogen (E2) increased GREB1 mRNA level to 1.69 fold of the control. ATA at 6 μM effectively inhibited the estrogen-induced increase of GRBE1 level, and even further decrease the GREB1 level to about 50% of the control. This inhibition effect of ATA is thus comparable with that of tamoxifen. Hence, it can be overall concluded that the strong inhibitory effect of ATA on ER-positive breast cancer cells is due to ATA-induced ERα degradation as well as ESR1 mRNA reduction and subsequent inhibition on ERα-responsive gene expression.

Example 15

Effect of ATA on ER Positive/HER2 Positive Breast Cancer Cells

Figure 10:
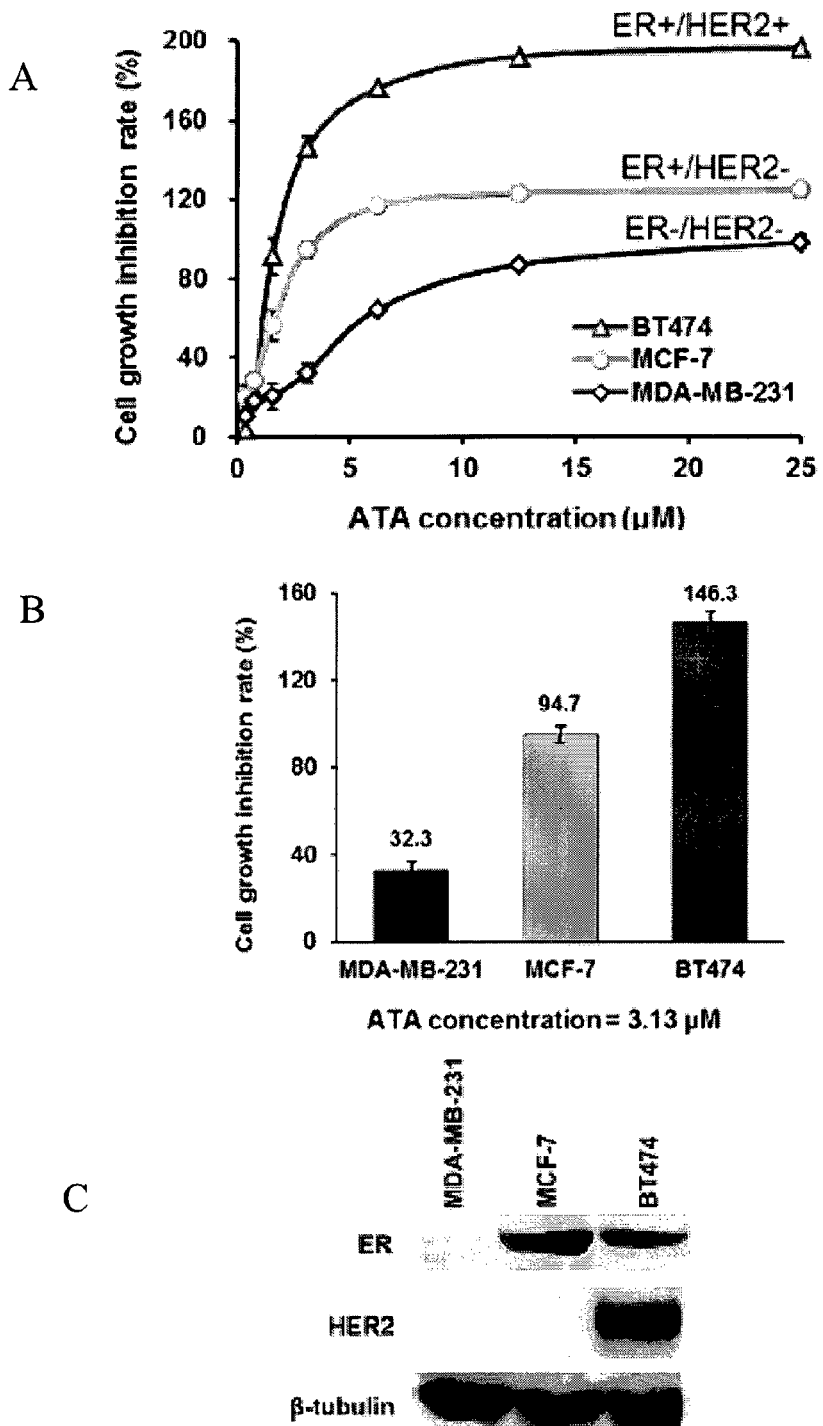
FIG. 10 shows growth inhibition rates of ATA measured in ER−/HER2− MDA-MB-231, ER+/HER2− MCF-7, and ER+/HER2+ BT474 breast cancer cells after 72 h of ATA treatment at different concentrations (A) and at 3.13 μM (B) by MTT assay. (C) Western blot results showing different levels of ERα and HER2 proteins in three breast cancer cell lines. The β-tubulin protein was probed as a loading control.
Figure 11:
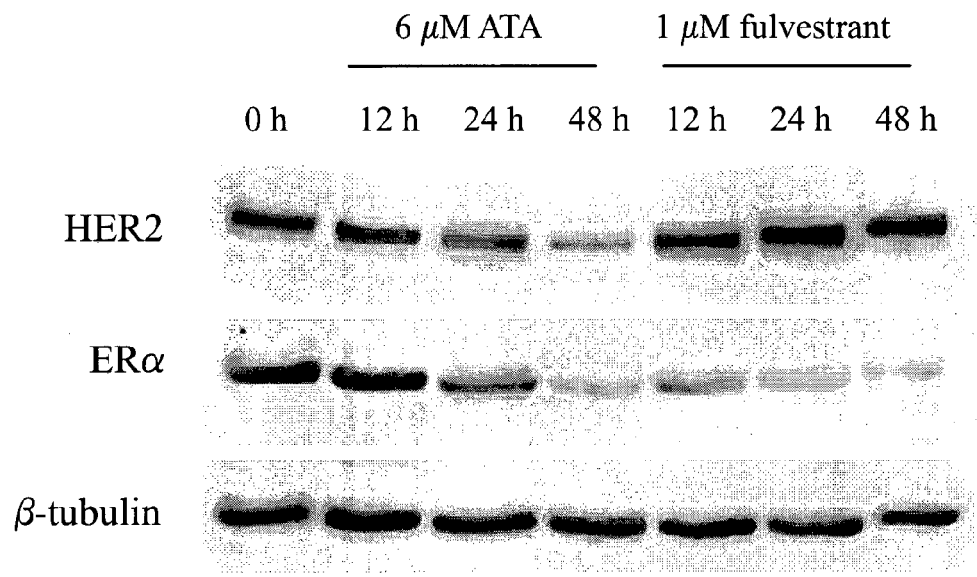
FIG. 11 shows that ATA reduced the level of ERα and HER2 in breast cancer BT474 cells. Fulvestrant only reduced ERα, but not HER2. Cells were treated with 6 μM ATA or 1 μM fulvestrant for indicated times and analyzed by Western blotting.

Surprisingly, it was furthermore discovered that ATA displayed very strong growth inhibition effect on BT474 breast cancer cells, which are ER positive with very high level of HER2 protein (FIG. 10C). It was found that ATA displayed much stronger growth inhibition effect in HER2+ than HER2− cells (FIG. 10A). Specifically, the growth inhibition rate of ATA at 3.13 µM increased from 32.3% in double negative 231 cells to 94.7% in HER2− MCF-7 cells and reached to the highest of 146.3% in HER2+ BT474 cells (FIG. 10B). This result suggests that ATA has specific growth inhibition ability on ER+/HER2+ breast cancer cells. Furthermore, the $IC_{50}$ value of ATA reduced to 1.0 µM in ER+/HER2+ breast cancer BT474 cells, which is 6.2 times lower than the $IC_{50}$ value of tamoxifen (6.20±0.10 µM). Finally, we found that ATA can reduce the level of HER2 protein in human breast cancer BT474 cells that over-express HER2 (FIG. 11). Taken together, these results show that ATA is more potent than tamoxifen in inhibiting the growth of both types of breast cancers: positive in ER and/or over-expression in HER2 protein.

The content of all documents cited herein is incorporated by reference in their entirety.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by a preferred embodiment, modification and variation of the invention herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are in the following claims. In addition, where features or aspects of the invention are described in terms of Markush groups, those skilled in the art will recognize that the invention is also thereby described in terms of any individual member or subgroup of members of the Markush group.

What is claimed is:

1. A method for inhibiting estrogen receptor signaling in a cell, comprising contacting said cell with an effective amount of a compound of Formula I

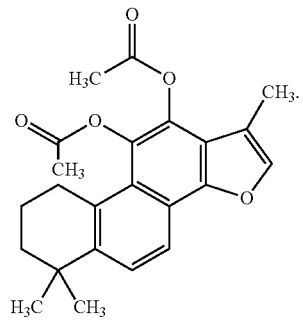

Formula I

2. The method of claim 1, wherein estrogen receptor signaling is inhibited by estrogen receptor protein degradation, reduced estrogen receptor mRNA levels and/or inhibition of estrogen receptor-responsive gene expression.

3. The method of claim 1, wherein HER2 expression is reduced in the cell after contacting said cell with an effective amount of a compound of Formula I

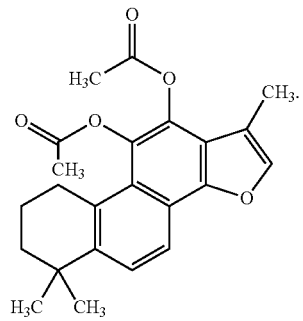

Formula I

4. The method of claim 3, wherein the cell is an estrogen receptor positive/HER2 positive (ER+/HER2+) breast cancer cell.

5. A method for inducing apoptosis in a cell, comprising contacting said cell with an effective amount of a compound of Formula I

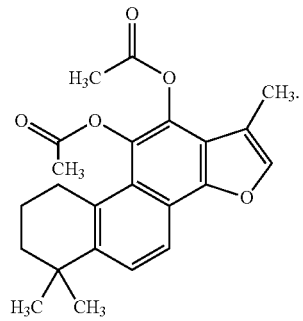

Formula I

6. The method of claim 5, wherein apoptosis is induced by generation of reactive oxygen species.

7. A method for treating cancer selected from breast cancer, cervical cancer, lung cancer, liver cancer, colorectal adenocarcinoma, neuroblastoma, melanoma, and leukemia in a subject, comprising administering an effective amount of a compound of Formula I to a subject in need thereof Formula I

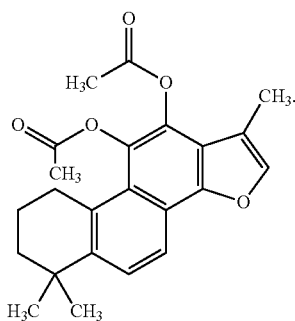

8. The method of claim 7, wherein the cancer is estrogen receptor-positive (ER+) breast cancer.

9. The method of claim 7, wherein the cancer is HER2 positive (HER2+) breast cancer.

10. The method of claim 7, wherein the method further comprises administering a second anticancer agent to the subject.

11. The method of claim 10, wherein the second anticancer agent is administered before, together with or after the compound of Formula I.

12. The method of claim 10, wherein the second anticancer agent is selected from the group consisting of paclitaxel, doxorubicin, herceptin, lapatinib, gefitinib, erlotinib, tamoxifen, fulvestrant, anastrazole, lectrozole, exemestane, fadrozole and combinations thereof.

13. The method of claim 7, wherein the subject has prior to administration of the compound of Formula I underwent anticancer therapy with a different anticancer agent or anticancer agent combination.

14. The method of claim 7, wherein the subject has previously been treated with an anticancer agent selected from the group of selective estrogen receptor modulators, estrogen receptor down regulators, aromatase inhibitors, HER2 inhibitors, anthracyclines, and combinations thereof.

15. The method of claim 14, wherein the anticancer agent is selected from the group consisting of doxorubicine, paclitaxel, herceptin, lapatinib, gefitinib, erlotinib, tamoxifen, fulvestrant, anastrazole, lectrozole, exemestane, fadrozole and combinations thereof.

16. The method of claim 13, wherein the subject has failed the previous therapy.

17. The method of claim 13, wherein the subject has developed resistance to one or more of the previously used anticancer agents.

18. The method of claim 7, wherein the subject is a mammal.

19. The method of claim 7, wherein the subject is a human.

* * * * *